(12) United States Patent
Zhang et al.

(10) Patent No.: US 10,900,079 B2
(45) Date of Patent: Jan. 26, 2021

(54) FINE-TUNED ULTRASPECIFIC NUCLEIC ACID HYBRIDIZATION PROBES

(71) Applicant: WILLIAM MARSH RICE UNIVERSITY, Houston, TX (US)

(72) Inventors: David Yu Zhang, Houston, TX (US); Juexiao Wang, Houston, TX (US); Ruojia Wu, Houston, TX (US)

(73) Assignee: William Marsh Rice University, Houston, TX (US)

( * ) Notice: Subject to any disclaimer, the term of this patent is extended or adjusted under 35 U.S.C. 154(b) by 373 days.

(21) Appl. No.: 15/174,373

(22) Filed: Jun. 6, 2016

(65) Prior Publication Data

US 2016/0340727 A1 Nov. 24, 2016

Related U.S. Application Data

(63) Continuation of application No. PCT/US2014/052827, filed on Aug. 27, 2014.
(Continued)

(51) Int. Cl.
| | | |
|---|---|---|
| *C07H 21/00* | (2006.01) | |
| *C12Q 1/6876* | (2018.01) | |
| *C07H 21/04* | (2006.01) | |
| *C12Q 1/6883* | (2018.01) | |

(52) U.S. Cl.
CPC ............ *C12Q 1/6876* (2013.01); *C07H 21/00* (2013.01); *C07H 21/04* (2013.01); *C12Q 1/6883* (2013.01); *C12Q 2600/112* (2013.01)

(58) Field of Classification Search
CPC .................................. C12Q 1/68; C07H 21/00
See application file for complete search history.

(56) References Cited

U.S. PATENT DOCUMENTS

| | | | | |
|---|---|---|---|---|
| 9,284,602 | B2* | 3/2016 | Zhang | C12Q 1/6832 |
| 2004/0023269 | A1* | 2/2004 | Li | C12Q 1/6844 |
| | | | | 435/6.18 |

(Continued)

FOREIGN PATENT DOCUMENTS

WO 2012058488 5/2012

OTHER PUBLICATIONS

Bonnet et al., Thermodynamic basis of the enhanced specificity of structured DNA probes. PNAS 96 :6171 (Year: 1999).*

(Continued)

*Primary Examiner* — Frank W Lu
(74) *Attorney, Agent, or Firm* — Parker Highlander PLLC

(57) ABSTRACT

Compositions and methods for highly specific nucleic acid probes and primers are provided. The probe system comprises a complement strand and a protector stand that form a partially double-stranded probe. The reaction standard free energy of hybridization between the probe and target nucleic acid as determined by Expression 1 ($\Delta G°_{rxn} = \Delta G°_{t-TC} - \Delta G°_{nh-PC} + (\Delta G°_{v-TC} - \Delta G°_{h-PC})$) is from about −4 kcal/mol to about +4 kcal/mol. Alternatively, the reaction standard free energy of hybridization between the probe and target nucleic acid is determined by Expression 1 to be within 5 kcal/mol of the standard free energy as determined by Expression 2 ($-R\tau \ln(([P]_0 - [C]_0)/[C]_0)$), where the $[P]_0$ term of Expression 2 equals the concentration of the protector strand and the $[C]_0$ term of Expression 2 equals the concentration of the complement strand. In addition, a method for on-the-fly fine tuning of a reaction using the present probe is provided.

12 Claims, 26 Drawing Sheets

Figure 1:
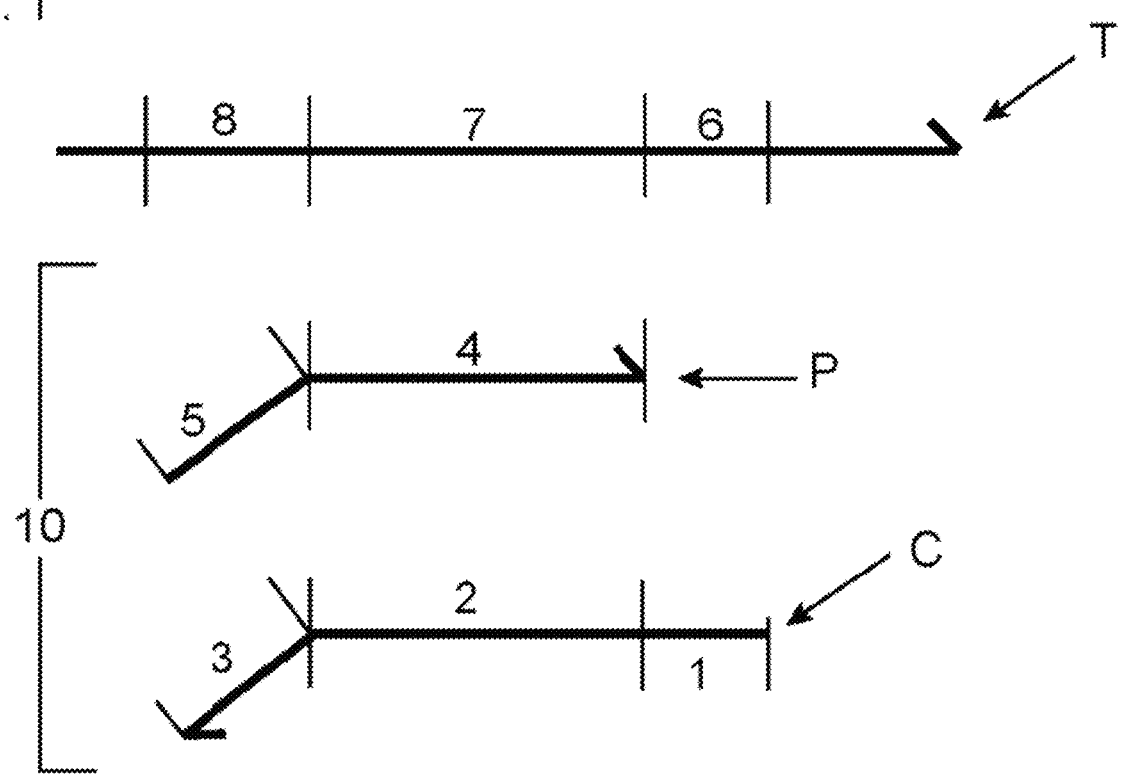

Specification includes a Sequence Listing.

Related U.S. Application Data

(60) Provisional application No. 61/916,321, filed on Dec. 16, 2013.

(56) References Cited

U.S. PATENT DOCUMENTS

| | | | | |
|---|---|---|---|---|
| 2005/0260635 | A1* | 11/2005 | Dirks | C12Q 1/6813 435/6.18 |
| 2007/0072215 | A1* | 3/2007 | Seelig | B82Y 10/00 435/6.11 |
| 2011/0306758 | A1 | 12/2011 | Zhang et al. | |
| 2013/0071839 | A1 | 3/2013 | Seelig et al. | |
| 2013/0274135 | A1* | 10/2013 | Zhang | C12Q 1/6832 506/9 |

OTHER PUBLICATIONS

Dirks et al., Thermodynamic Analysis of Interacting Nucleic Acid Strands SIAM Reviews 49(1), 65-88 (2007). (Year: 2007).*

Miller et al., Bacteriophage T4 Genome. Microbiology and Molecular Biology Reviews 67(1) : 86 (Year: 2003).*

SantaLucia et al. The Thermodynamics of DNA structural motifs. Ann. Rev. Biophys. Biomol. Struct. 33 :415 (Year: 2004).*

Li et al., A new class of homogeneous nucleic acid probes based on specific displacement hybridization. Nucleic Acids Research 30(2) :e5 (Year: 2002).*

European Supplementary Search Report dated Jun. 28, 2017 for European Patent Application No. 14873077.3.

Zhang David Yu et al: "Optimizing the specificity of nucleic acid hybridization", Nature Chemistry, Nature Publishing Group, UK, vol. 4, No. 3, Mar. 1, 2012 (Mar. 1, 2012), pp. 208-214.

David Yu Zhang et al: "Optimizing the specificity of nucleic acid hybridization", Nature Chemistry, vol. 4, No. 3, Jan. 22, 2012 (Jan. 22, 2012), pp. 208-214.

Gregoire Al Tan-Bonnet et al: "Nucleic acid hybridization: Robust sequence discrimination", Nature Chemistry, vol. 4, No. 3, Feb. 21, 2012 (Feb. 21, 2012), pp. 155-157.

Sherry Xi Chen et al: "Conditionally fluorescent molecular probes for detecting single base changes in double-stranded DNA", Nature Chemistry, vol. 5, No. 9, Jul. 28, 2013 (Jul. 28, 2013), pp. 782-789.

* cited by examiner

SEQUENCE LISTING

<160> NUMBER OF SEQ ID NOS: 70

<210> SEQ ID NO 1
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
cuuuacccag guuuuaau                                                      18

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aaaacctggg taaag                                                         15

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
acttttaaga agtgagcggt ggcggtg                                        27

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
gccaccaccg ccaccgctca cttcttaaaa gt                                  32

<210> SEQ ID NO 5
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
auggcggcgc ugagcggugg cggugguggc ggcgcggagc                          40

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
caaaatgaac agcccgaggc cggcgc                                         26

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
gccggcgccg gcctcgggct gttcattttg                                     30

<210> SEQ ID NO 8
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
ggggacaugg agcccgaggc cggcgccggc gccggcgccg                          40

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Synthetic probe

<400> SEQUENCE: 9
gacatgtcgc ggaggaggtg tggaatatc                                29

<210> SEQ ID NO 10
<211> LENGTH: 39
<212> TYPE: DNA
<213> ORGANISM: Artificial Sequence
<220> FEATURE:
<223> OTHER INFORMATION: Description of Artificial Sequence: Synthetic probe

<400> SEQUENCE: 10
tcatttgttt gatattccac acctcctccg cgacatgtc                     39

<210> SEQ ID NO 11
<211> LENGTH: 50
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 11
ccugccauuc cggaggaggu guggaauauc aaacaaauga uuaaguugac          50

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: Synthetic probe

<400> SEQUENCE: 12
catgctggtg tattggacaa atttggtgg                                29

<210> SEQ ID NO 13
<211> LENGTH: 40
<212> TYPE: DNA
<213> ORGANISM: Artificial Sequence
<220> FEATURE:
<223> OTHER INFORMATION: Description of Artificial Sequence: Synthetic probe

<400> SEQUENCE: 13
gattatgctc cccaccaaat tgtccaata caccagcatg                     40

<210> SEQ ID NO 14
<211> LENGTH: 50
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 14
auagaggccc uauuggacaa auuuggguggg gagcauaauc caccaucaau        50

<210> SEQ ID NO 15

```
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
gcacggattc ccaatacacc agcaagcta                                    29

<210> SEQ ID NO 16
<211> LENGTH: 42
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
gttggagtgc atctagcttg ctggtgtatt gggaatccgt gc                     42

<210> SEQ ID NO 17
<211> LENGTH: 50
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
gccuaugaag aauacaccag caagcuagau gcacuccaac aaagagaaca             50

<210> SEQ ID NO 18
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
gcttcatgga acggaactga tttttctgtt tctag                             35

<210> SEQ ID NO 19
<211> LENGTH: 47
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
attgatgcag agctagaaac agaaaaatca gttccgttcc atgaagc                47

<210> SEQ ID NO 20
<211> LENGTH: 55
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
aaaaacaagu ggaacggaac ugauuuuucu guuucuagcu cugcaucaau aaugu       55

<210> SEQ ID NO 21
<211> LENGTH: 32
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
acgcgccttg gatttgcatg gcacggagca ac                                    32

<210> SEQ ID NO 22
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
tttgtggtga cttggggttg ctccgtgcca tgcaaatcca aggcgcgt                   48

<210> SEQ ID NO 23
<211> LENGTH: 50
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
cccacagaug uggcacggag caaccccaag ucaccacaaa aaccuaucgu                 50

<210> SEQ ID NO 24
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
gacagtggta cctgcaaggt gtgcgctaac tc                                    32

<210> SEQ ID NO 25
<211> LENGTH: 39
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25
gagttagcgc acaccttgca ggtaccactg tcctctgtt                             39

<210> SEQ ID NO 26
<211> LENGTH: 50
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
cugcccaaca aacagaggac agugguaccu gcaaggugug gaguuacagu                 50

<210> SEQ ID NO 27
<211> LENGTH: 36
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 27
gactccacta tctcactgat gatagagagg tctaat                               36

<210> SEQ ID NO 28
<211> LENGTH: 43
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
actctgggat tagacctctc atcatcagtg agatagtgga gtc                       43

<210> SEQ ID NO 29
<211> LENGTH: 50
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
cuaaagaaag cacugaugau gagaggucua aucccagagu gcugugcugu                50

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
ttgctacaga agaaaccaat t                                               21

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
ccaaccaatt ggtttcttct gtagcaa                                         27

<210> SEQ ID NO 32
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
caggauggag agaagaaacc aauugguugg gacacugaua                           40

<210> SEQ ID NO 33
<211> LENGTH: 29
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 33
ctgaacaagg ttggaagtgt tggagaatg                                       29

<210> SEQ ID NO 34
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 34
ttgtaagtgg aacattctcc aacacttcca accttgttca g                         41

<210> SEQ ID NO 35
<211> LENGTH: 50
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
gaauugcaug uggaaguguu ggagaauguu ccacuuacaa cacacaacuu                50

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 36
tcgaggagct ggatacagct g                                               21

<210> SEQ ID NO 37
<211> LENGTH: 37
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 37
ctgtactctt ctcgtccagc tgtatccagc tcctcga                              37

<210> SEQ ID NO 38
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gacatactgg atacagctgg acgagaagag tacagtgcc                            39

<210> SEQ ID NO 39
<211> LENGTH: 29
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 39
ctggatacag ctggacgaga agagtacag                                     29

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
cgagaagagt acagccgagg ag                                            22

<210> SEQ ID NO 41
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ctcctcggct gtactcttct cgtccagctg tatccag                            37

<210> SEQ ID NO 42
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
atactggata cagctggaca tgaagagtac ag                                 32

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
catgaagagt acagccggag tacg                                          24

<210> SEQ ID NO 44
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
aacatgcacg ctgtactctt catgtccagc tgtatccagt at                      42

<210> SEQ ID NO 45
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 45
acatactgga tacagctgga aaagaagagt acag        34

<210> SEQ ID NO 46
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ggaaaagaag agtacagcgt gcatgtt        27

<210> SEQ ID NO 47
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
aacatgcacg ctgtactctt cttttccagc tgtatccagt atgt        44

<210> SEQ ID NO 48
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
catactggat acagctggac tagaagagta cag        33

<210> SEQ ID NO 49
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gactagaaga gtacagcctt ctgcagt        27

<210> SEQ ID NO 50
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
actgcagaag gctgtactct tctagtccag ctgtatccag tatg        44

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 51
cactcattca ataccctacg tcac                                          24

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 52
tcaaacccac tcattcaata ccc                                           23

<210> SEQ ID NO 53
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 53
gtgacgtagg gtattgaatg agtgggtttg a                                  31

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 54
taccaaccac tcattcaata ccct                                          24

<210> SEQ ID NO 55
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 55
gtgacgtagg gtattgaatg agtggttggt a                                  31

<210> SEQ ID NO 56
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 56
tttcatccac tcattcaata ccctac                                        26

<210> SEQ ID NO 57
<211> LENGTH: 31
<212> TYPE: DNA
<213> ORGANISM: Artificial Sequence
<220> FEATURE:
<223> OTHER INFORMATION: Description of Artificial Sequence: Synthetic
      probe
```

<400> SEQUENCE: 57
gtgacgtagg gtattgaatg agtggatgaa a                            31

<210> SEQ ID NO 58
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 58
ttctactcca ctcattcaat accctac                                 27

<210> SEQ ID NO 59
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 59
gtgacgtagg gtattgaatg agtggagtag aa                           32

<210> SEQ ID NO 60
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
uggaguguga cauggguguu ug                                      22

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 61
aagcatgtgg agtgtgacaa t                                       21

<210> SEQ ID NO 62
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 62
caaacaccat tgtcacactc cacatgctt                               29

<210> SEQ ID NO 63
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 63
agatgggtgg agtgtgaca                                                    19

<210> SEQ ID NO 64
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 64
caaacaccat tgtcacactc cacccatct                                         29

<210> SEQ ID NO 65
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 65
agctttagtg gagtgtgaca atg                                               23

<210> SEQ ID NO 66
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 66
caaacaccat tgtcacactc cactaaagct                                        30

<210> SEQ ID NO 67
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 67
aggaaagtgg agtgtgacaa tg                                                22

<210> SEQ ID NO 68
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 68
caaacaccat tgtcacactc cactttcct                                         29

<210> SEQ ID NO 69
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 69

```
atgtatagtg gagtgtgaca atgg                                           24

<210> SEQ ID NO 70
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 70
caaacaccat tgtcacactc cactatacat                                     30
```

FINE-TUNED ULTRASPECIFIC NUCLEIC ACID HYBRIDIZATION PROBES

CROSS REFERENCE TO RELATED APPLICATIONS

The present application is a Continuation application of International Application No. PCT/US14/52827, filed Aug. 27, 2014, which claims priority to U.S. Provisional Application No. 61/916,321 filed Dec. 16, 2013, which is incorporated herein by reference in its entirety.

BACKGROUND

Small differences in DNA and RNA sequence can lead to big differences in health. For example, a single-base change in a bacterial genome can lead to antibiotic resistance, and a single-base change in a human genome can lead to cancer remission. With the maturation of the genomics field and the accompanying discovery of many nucleic acid biomarker sequences and molecules, there is a strong demand from the biotechnology industry to develop reliable, robust, inexpensive, and precise nucleic acid assays that can discriminate single-base changes. Enzyme-based discrimination methods for nucleic acid sequence differences are difficult to integrate with a wide variety of technologies because enzymes demand specific temperatures and buffer conditions.

Enzyme-free techniques to ensure highly specific hybridization of nucleic acids to their complements has traditionally relied on the optimization of melting temperature, but this is difficult to precisely predict and control. Recently, toehold hybridization probes have been demonstrated in which single-base changes in nucleic acid sequences can be robustly discriminated across a wide range of temperatures and salinities. These probes are designed to react with their intended targets with reaction standard free energy ($\Delta G°_{rxn}$) close to zero, so that hybridization yield is close to 50% for the intended target. A variant of the target that differs by even a single nucleotide will bind to the probe with significantly less yield (median 2%).

To achieve the $\Delta G°_{rxn} \approx 0$ property, these probes balance the binding energies of a target-specific "toehold" region with that of a target-nonhomologous "balance" region. DNA probes have been experimentally demonstrated to function robustly to discriminate DNA targets, and RNA probes have been experimentally demonstrated to function robustly to discriminate RNA targets.

These probes, however, suffer from several limitations. For example, when the probe and the target are of different forms, such as when DNA probes are designed specifically to RNA targets, 2'-O-methyl RNA probes are designed to bind RNA targets, and when LNA probes are designed to specifically bind DNA targets, the differences in hybridization thermodynamics between nucleic acid molecules of different forms result in poor probe design, with either low specificity or low sensitivity. Additionally, the thermodynamic binding strength of individual base pairs/stacks are relatively large, practically precluding fine-tuning of the reaction $\Delta G°_{rxn}$, which in turn limits the tunability of the tradeoff between probe system specificity and sensitivity. Furthermore, published DNA and RNA hybridization thermodynamic parameters are known to be incomplete and/or inaccurate in certain conditions. An in silico designed probe system may possess a real $\Delta G°_{rxn}$ that differs significantly from the calculated $\Delta G°_{rxn}$; without a method of fine-tuning probe performance, iterative trial-and-error must be employed to achieve an optimal probe design with the desired $\Delta G°_{rxn}$.

SUMMARY

The present disclosure provides, according to certain instances, highly specific nucleic acid hybridization probe systems, which reliably discriminate single-base changes in target nucleic acids. Compared to previous work, the probe systems described in the present disclosure excel in (1) reliably probing DNA, RNA, and modified nucleic acid targets with DNA, RNA, and other nucleic acid probes, and (2) enabling fine-tuning of the tradeoff between sensitivity and specificity. The compositions and methods of the present disclosure may be useful in, among other things, molecular cancer diagnostics, infectious disease diagnostics, food safety diagnostics, and research discovery tools based on DNA and RNA detection and quantification.

In one instance, a composition for selective interaction with a target nucleic acid molecule is provided. The composition comprises a first concentration of a first nucleic acid strand comprising a first region, second region, and third region, and a second concentration of a second nucleic acid strand comprising a fourth region and fifth region. The target nucleic acid comprises a sixth and seventh region of a nucleotide sequence that is at least partially, if not fully, complementary to a nucleotide sequence of the first and second regions, respectively. The first and second concentrations are such that the interaction between the target nucleic acid and the composition possesses a standard free energy ($\Delta G°_{rxn}$) as determined by Expression 1 [$\Delta G°_{rxn} = \Delta G°_{t\text{-}TC} - \Delta G°_{nh\text{-}PC} + (\Delta G°_{v\text{-}TC} - \Delta G°_{h\text{-}PC})$] within 5 kcal/mol of a standard free energy as determined by Expression 2 ($-R\tau \ln(([P]_0-[C]_0)/[C]_0)$), where the $[P]_0$ term of Expression 2 equals the second concentration, and the $[C]_0$ term of Expression 2 equals the first concentration, R equals the universal gas constant 8.314 J/mol·K, and $\tau$ equals the temperature in Kelvin. In this instance, the $\Delta G°_{t\text{-}TC}$ term of Expression 1 represents the standard free energy of hybridization between the sixth region and the first region; the $\Delta G°_{nh\text{-}PC}$ term of Expression 1 represents the free energy of hybridization between the fifth region and the third region; the $\Delta G°_{v\text{-}TC}$ term of Expression 1 represents the standard free energy of hybridization between the seventh region and the second region; and the $\Delta G°_{h\text{-}PC}$ term of Expression 1 represents the standard free energy of hybridization between the fourth region and the second region. The method of calculating $\Delta G°$ values is described in detail later in the description. In certain instances, the concentration of the target nucleic acid is smaller than the first concentration. In certain other instances, the concentration of the target nucleic acid is equal to or greater than the first concentration.

In another instance, the sequences of the first, second, third, fourth, fifth, sixth, and seventh regions are such that the interaction between the target nucleic acid and the composition possesses a standard free energy ($\Delta G°_{rxn}$) as determined by Expression 1 [$\Delta G°_{rxn} = \Delta G°_{t\text{-}TC} - \Delta G°_{nh\text{-}PC} + (\Delta G°_{v\text{-}TC} - \Delta G°_{h\text{-}PC})$] of about $-4$ kcal/mol and $+4$ kcal/mol, while [$\Delta G°_{t\text{-}TC} - \Delta G°_{nh\text{-}PC}$] is not between $-1$ kcal/mol and $+1$ kcal/mol. In other instances, the values of $\Delta G°_{t\text{-}TC}$ and $\Delta G°_{nh\text{-}PC}$ are not within 10% of each other.

In another instance, the target nucleic acid further comprises an eighth region adjacent to the seventh region, such that the eighth region nucleotide sequence is not complementary to the third region nucleotide sequence, with fewer than 50% of the aligned nucleotides paired between the eighth and the third region at equilibrium.

In another instance, a process for creating a nucleic acid probe is provided. The process comprises the following steps: selecting a target nucleotide sequence in a nucleic acid molecule, the target nucleotide sequence comprising a sixth nucleotide subsequence and a seventh nucleotide subsequence; selecting a first nucleotide sequence comprising a first nucleotide subsequence, a second nucleotide subsequence, and a third nucleotide subsequence; and selecting a second nucleotide sequence comprising a fourth nucleotide subsequence and a fifth nucleotide subsequence. In this instance, the steps of selecting the first, second, and target nucleotide sequences are based on the interactions between such possessing a standard free energy from about $-4$ kcal/mol to about $+4$ kcal/mol as determined by Expression 1 $[\Delta G°_{rxn} = \Delta G°_{t-TC} - \Delta G°_{nh-PC} + (\Delta G°_{v-TC} - \Delta G°_{h-PC})]$, wherein the $\Delta G°_{t-TC}$ term of Expression 1 represents the standard free energy of hybridization between the sixth region and the first region, wherein the $\Delta G°_{nh-PC}$ term of Expression 1 represents the free energy of hybridization between the fifth region and the third region, wherein the $\Delta G°_{v-TC}$ term of Expression 1 represents the standard free energy of hybridization between the seventh region and the second region, and wherein the $\Delta G°_{h-PC}$ term of Expression 1 represents the standard free energy of hybridization between the fourth region and the second region. The process further comprises the step of synthesizing a first nucleotide strand comprising the first nucleotide sequence and a second nucleotide strand comprising the second nucleotide sequence.

In addition to selection of the relevant nucleotide sequences based on Expression 1, the process may alternatively or further comprise selecting the first and second concentrations such that the standard free energy as determined by Expression 2 $(-R\tau \ln(([P]_0-[C]_0)/[C]_0))$ is within 5 kcal/mol of the standard free energy as determined by Expression 1 $(\Delta G°_{rxn})$ where the terms $[C]_0$ and $[P]_0$ of Expression 2 represent a predetermined concentration of the first nucleotide strand and the second nucleotide strand, respectively, R equals the universal gas constant 8.314 J/mol·K, and $\tau$ equals the temperature in Kelvin. In one instance, if the standard free energy as determined by Expression 1 is not within 5 kcal/mol of the standard free energy as determined by Expression 2, then the predetermined concentration of at least one of the first nucleic acid strand or the second nucleic acid strand may be modified until this condition is met. Alternatively, optimization may occur by repeating the steps of the process and selecting modified nucleotide sequences that meet the desired free energy conditions.

A method for identifying the presence or quantity of a nucleic acid molecule bearing the target nucleotide sequence in a sample is provided. The method comprises applying a probe to a sample possibly comprising a target nucleic acid molecule and operating the hybridization reaction at a temperature from about 4° C. to about 75° C., from about 25° C. to about 70° C., or from about 37° C. to about 65° C., or any temperature range there between, to permit hybridization of the probe to the target nucleic acid molecule, if the target nucleic acid molecule is present in the sample. In this instance, the probe comprises a first nucleic acid strand and a second nucleic acid strand. The first nucleic acid strand comprises a first region, a second region, and a third region, wherein the first region possesses a nucleotide sequence that is complementary to a nucleotide sequence of a sixth region of the target nucleic acid molecule, and wherein the second region possesses a nucleotide sequence that is complementary to a nucleotide sequence of a seventh region of the target nucleic acid molecule. The second nucleic acid strand comprising a fourth region and a fifth region, wherein the fourth region possesses a nucleotide sequence that is complementary to the nucleotide sequence of the second region, and wherein the fifth region possesses a nucleotide sequence that is complementary to the nucleotide sequence of the third region. In one instance, the target nucleic acid molecule is RNA.

A method for selectively amplifying a target nucleic acid sequence from a sample, said method comprising applying the probe as an enzymatic primer to a mixture comprising the sample, a DNA or RNA polymerase, and a mixture of nucleotide triphosphates. In some instances, the mixture further comprises an additional DNA or RNA primer, or an additional enzyme, such as a nicking enzyme, a recombinase, a helicase, a restriction enzyme, a nuclease, or a ligase. In some instances, the combination of the probe and the mixture are allowed to react isothermally for between 1 minute and 72 hours. In some instances, the combination of the probe and the mixture are allowed to react through a number of temperature cycles, varying between 5 and 200 cycles.

The features and advantages of the present disclosure will be readily apparent to those skilled in the art upon a reading of the description of the instances that follows.

DRAWINGS

Some specific example instances of the disclosure may be understood by referring, in part, to the following description and the accompanying drawings.

FIG. 1 provides one embodiment of a suitable nucleic acid probe system 10 for use in the present invention. Probe system 10 comprises a complement strand C (also referred to herein as the "first strand") and a protector strand P (also referred to herein as the "second strand") designed with respect to a target nucleic acid T (also referred to as "target nucleic acid molecule," or "target nucleic acid strand"). Complement strand C includes a target-toehold-complementary region 1 (also referred to herein as the "first region"), a target-homologous complementary region 2 (also referred to herein as the "second region"), and a target-nonhomologous-complementary region 3 (also referred to herein as the "third region"). The protector comprises a target-homologous region 4 (also referred to herein as the "fourth region") and a target-nonhomologous region 5 (also referred to herein as the "fifth region"). The target comprises a target-toehold region 6 (also referred to herein as the "sixth region") and a target-validation region 7 (also referred to herein as the "seventh region"). In certain embodiments, the target may further comprise a target upstream region 8, and/or additional unnamed upstream and downstream regions. The target homologous region 4 of protector P may differ in sequence from the target validation region 7 of target T, for example in the instance protector P and target T are different types of nucleic acids (e.g., RNA vs. DNA). As used herein, the term "region" when referring to the probe system or target nucleic acid defines a group of contiguous nucleotide bases that act as a functional unit in hybridization and dissociation.

Figure 2A:
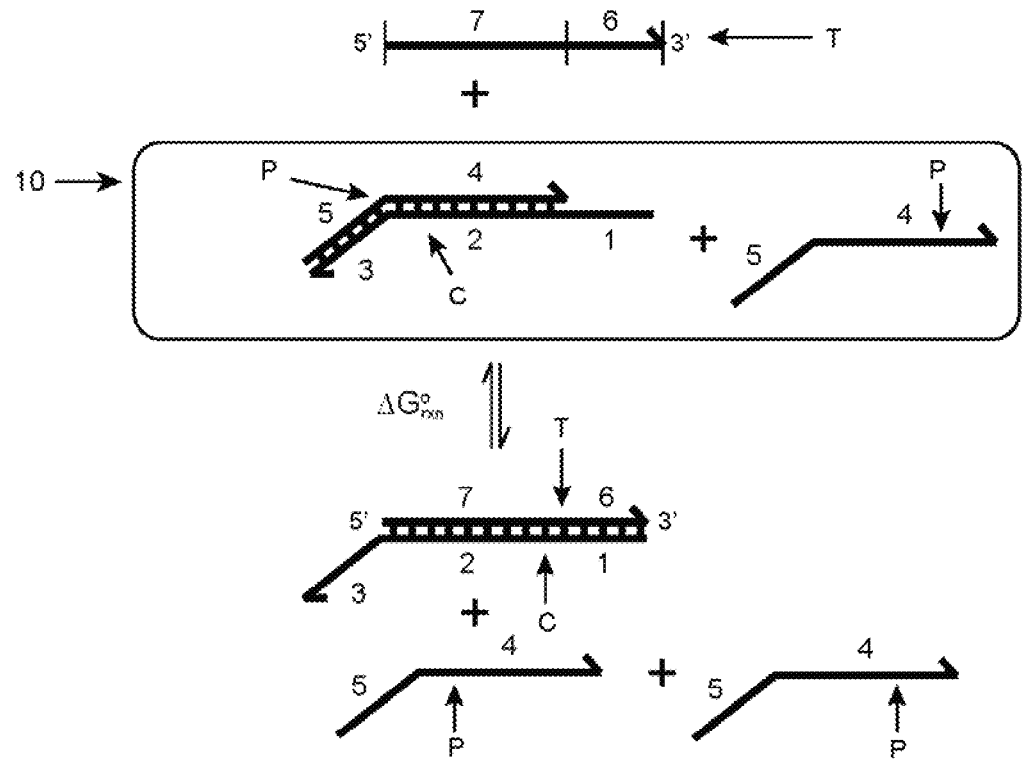
Figure 2B:
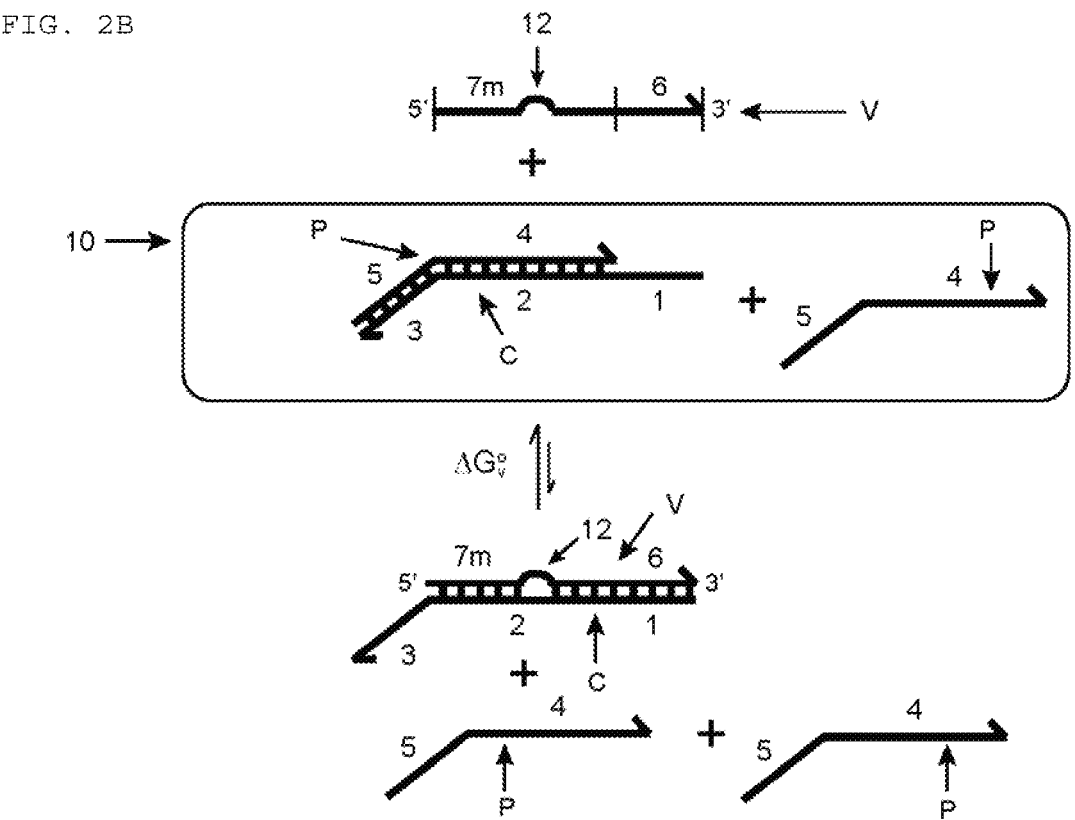

FIG. 2A provides an exemplary probe system 10 and its reaction with target nucleic acid T and FIG. 2B provides and exemplary probe system 10 and its reaction with a variant target V having a single-base difference 12 than target T in the target validation region 7. Referring now to FIG. 2A, probe system 10 is designed such that the standard free energy of the hybridization reaction of probe system 10 with intended target T ($\Delta G°_{rxn}$) is approximately equal to (−Rτ ln(([P]$_0$−[C]$_0$)/[C]$_0$)) (Expression 2), and ensures a medium to high yield of complement strand C bound to target T. Referring now to FIG. 2B, probe system 10 reacts with variant target V with a standard free energy $\Delta G°_V$ that is more positive than $\Delta G°_{rxn}$ by $\Delta\Delta G°_{SNP}$, (i.e., $\Delta G°_V$=$\Delta G°_{rxn}$+$\Delta\Delta G°_{SNP}$) where $\Delta\Delta G°_{SNP}$ denotes the relative thermodynamic penalty of the single base change. This results in probe system 10 having a much lower binding yield for variant target V due to the single base mismatch 12 as compared to the intended target T.

Figure 3:
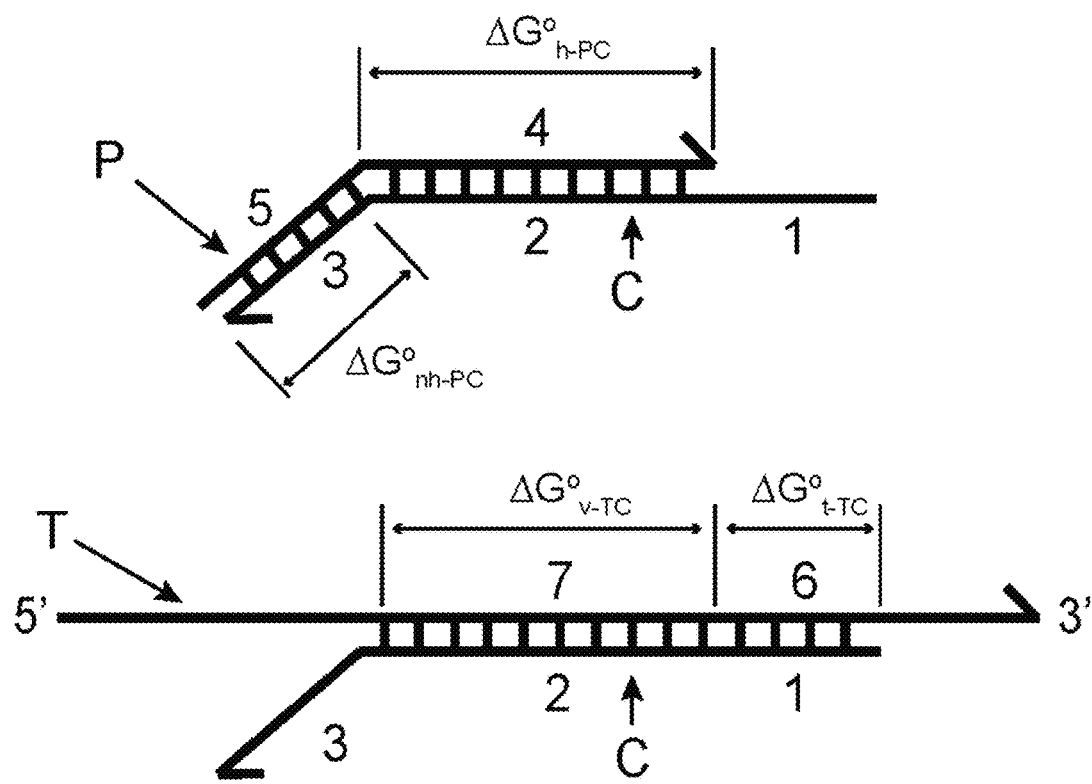

FIG. 3 provides the various standard free energies of the binding region components that are used in the present invention to calculate the reaction standard free energy ($\Delta G°_{rxn}$).

Figure 4:
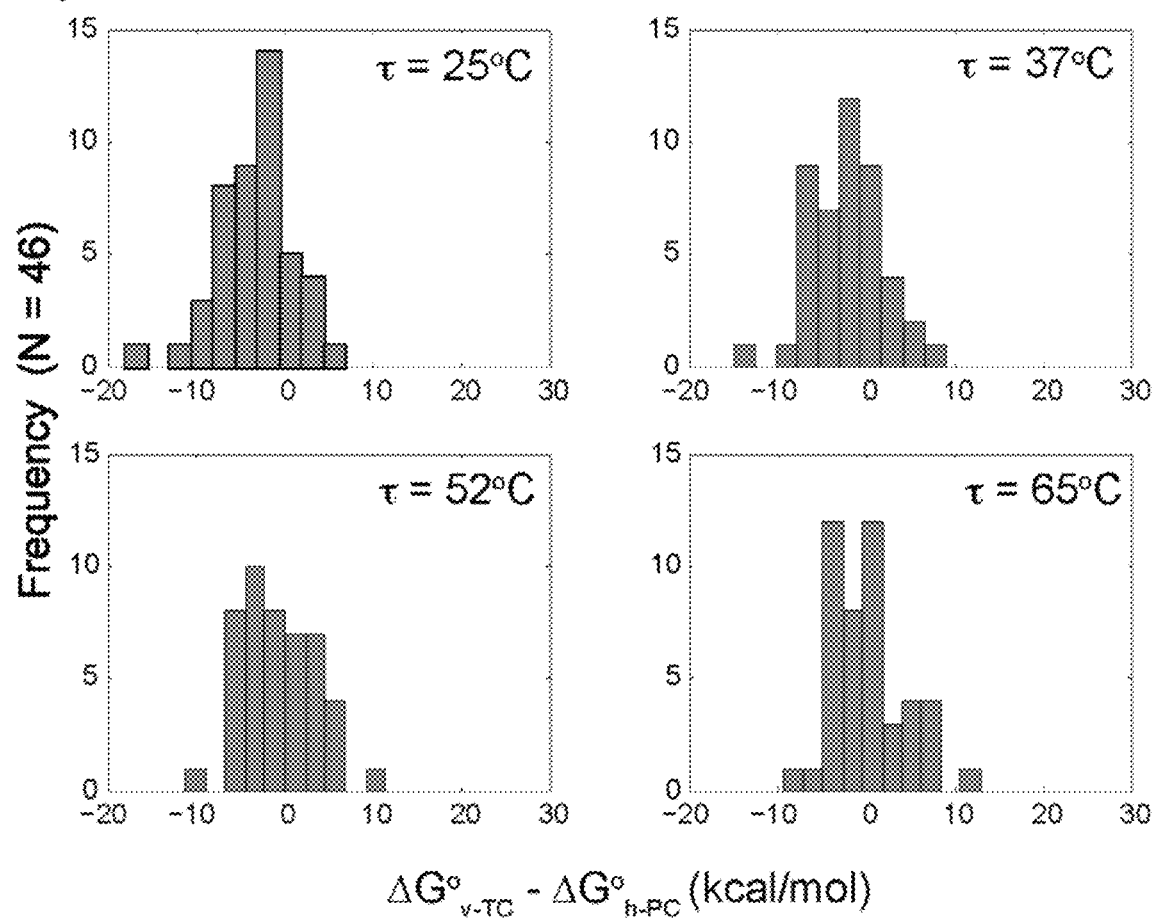

FIG. 4 provides a distribution of ($\Delta G°_{v-TC}$−$\Delta G°_{h-PC}$) values for 46 different 50 nt non-overlapping subsequences of BRAF expressed (exonic) mRNA at different temperatures, assuming that the first nucleic acid molecule and second nucleic acid molecules are both DNA. As can be seen, there is a wide spread, with the largest values over 20 kcal/mol greater than the smallest values. Considering that a 1.4 kcal/mol difference in $\Delta G°_{rxn}$ can lead to a factor of 10 difference in specificity or sensitivity, the results here demonstrate that the $\Delta G°_{v-TC}$−$\Delta G°_{h-PC}$ term should be considered in the design of the probes described herein and thereby improves upon prior art design parameters.

Figure 5:
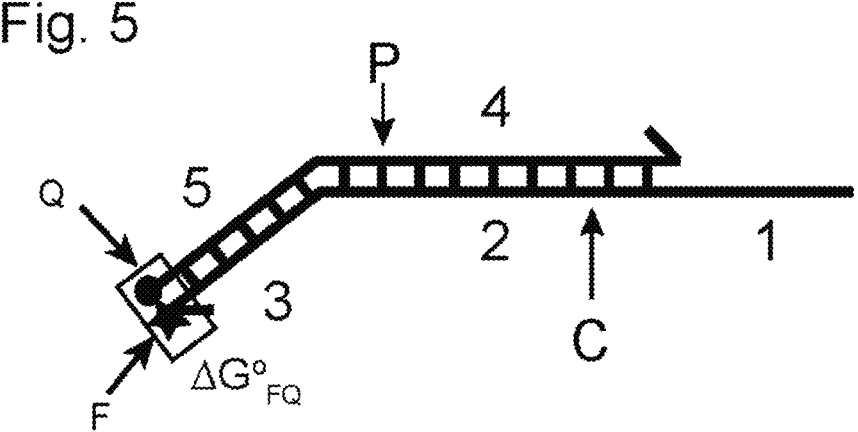
Figure 5:
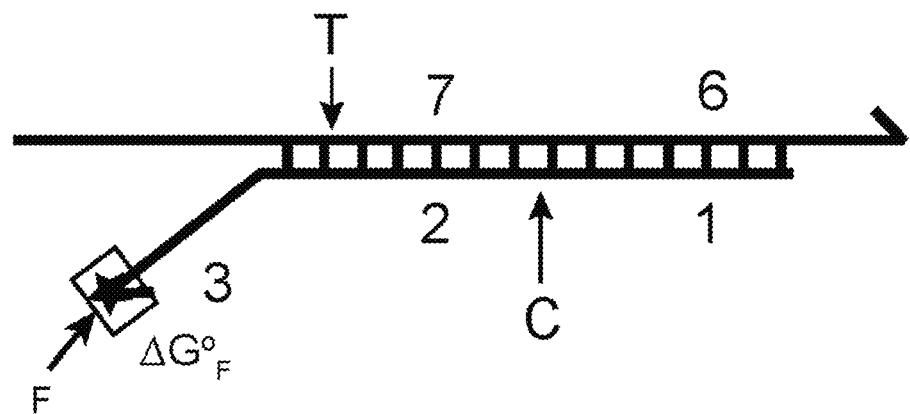

FIG. 5 provides the standard free energy contribution of differential label thermodynamics ($\Delta G°_{label}$=$\Delta G°_F$−$\Delta G°_{FQ}$). In this instance, the label of protector strand P is a quencher Q that is specific to fluorophore F of complement strand C.

Figure 6:
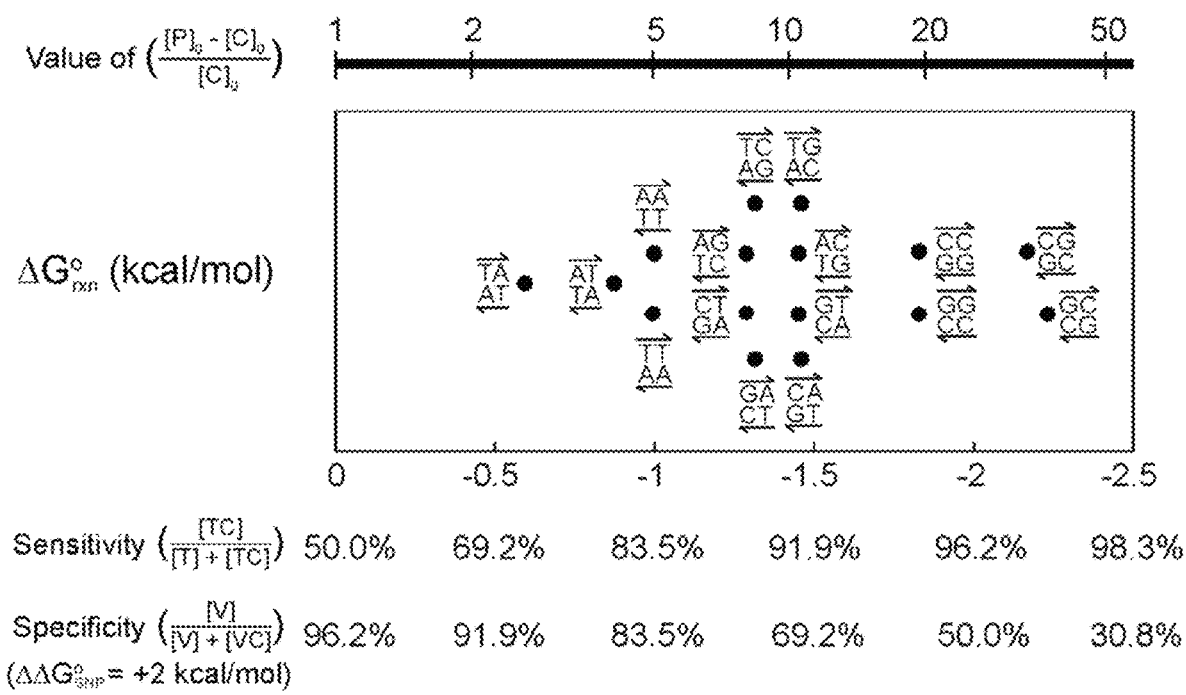

FIG. 6 is a representation of one aspect of the present method for tuning probe system behavior. Specifically, in addition to modulation of reaction standard free energy ($\Delta G°_{rxn}$) via addition or removal of base stacks (modification of value of Expression 1), modulation of stoichiometry (ratio of the concentrations of P to C) can be utilized to control the tradeoff between specificity and sensitivity of the probe and provides a more effective method of doing so (modifying the value of Expression 2). Here, the target concentration is assumed to be smaller than the first concentration, and the sensitivity is calculated as the equilibrium binding yield of the intended target [TC]/([T]+[TC]), and the specificity is calculated as one minus the binding yield of a target variant 1−[VC]/([V]+[VC])=[V]/([V]+[VC]). In this figure, the variant differs from the target by a single base, and possesses $\Delta\Delta G°_{SNP}$=+2 kcal/mol at 37° C. Modulating P to C stoichiometry is also beneficial when $\Delta G°_{rxn}$ cannot be accurately calculated in silico by allowing rescue of probe systems with real $\Delta G°_{rxn}$ that differs by up to 5 kcal/mol from their calculated $\Delta G°_{rxn}$.

Figure 7A:
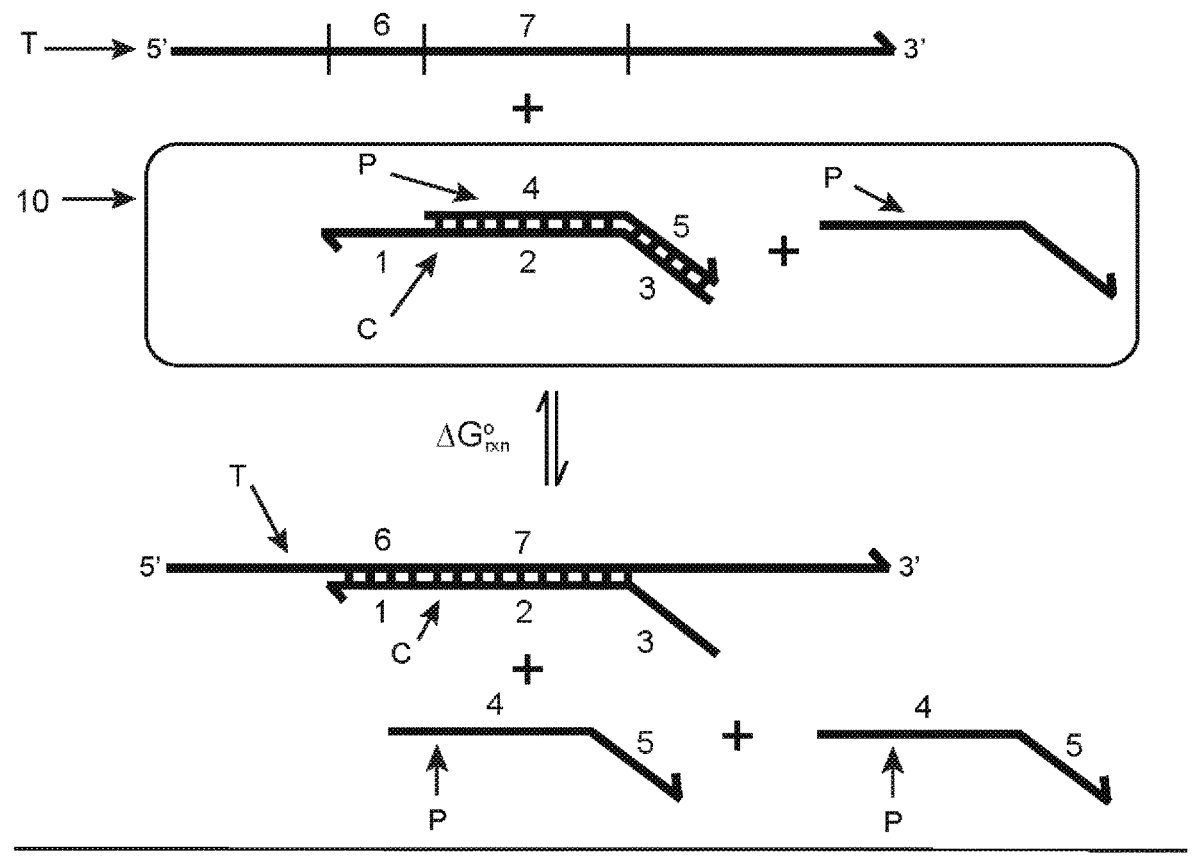
Figure 7B:
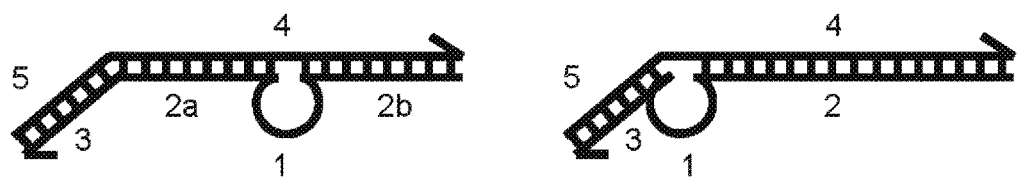
Figure 7C:
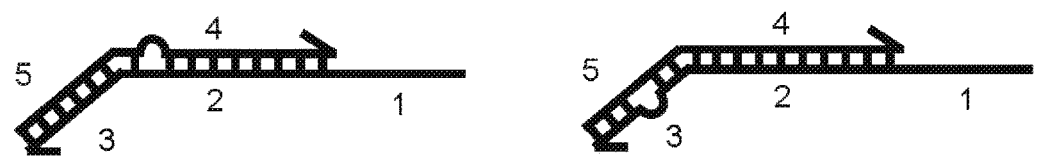

FIGS. 7A, 7B and 7C represent variant probe system designs. FIG. 7A represents a probe system with opposite 5'/3' orientation. FIG. 7B represents a probe system in which region 1 is embedded within region 2, or in which region 1 exists between regions 2 and 3. FIG. 7C represents a probe system in which regions 2 and 4 are not perfectly complementary, or in which regions 3 and 5 are not perfectly complementary.

Figure 8:
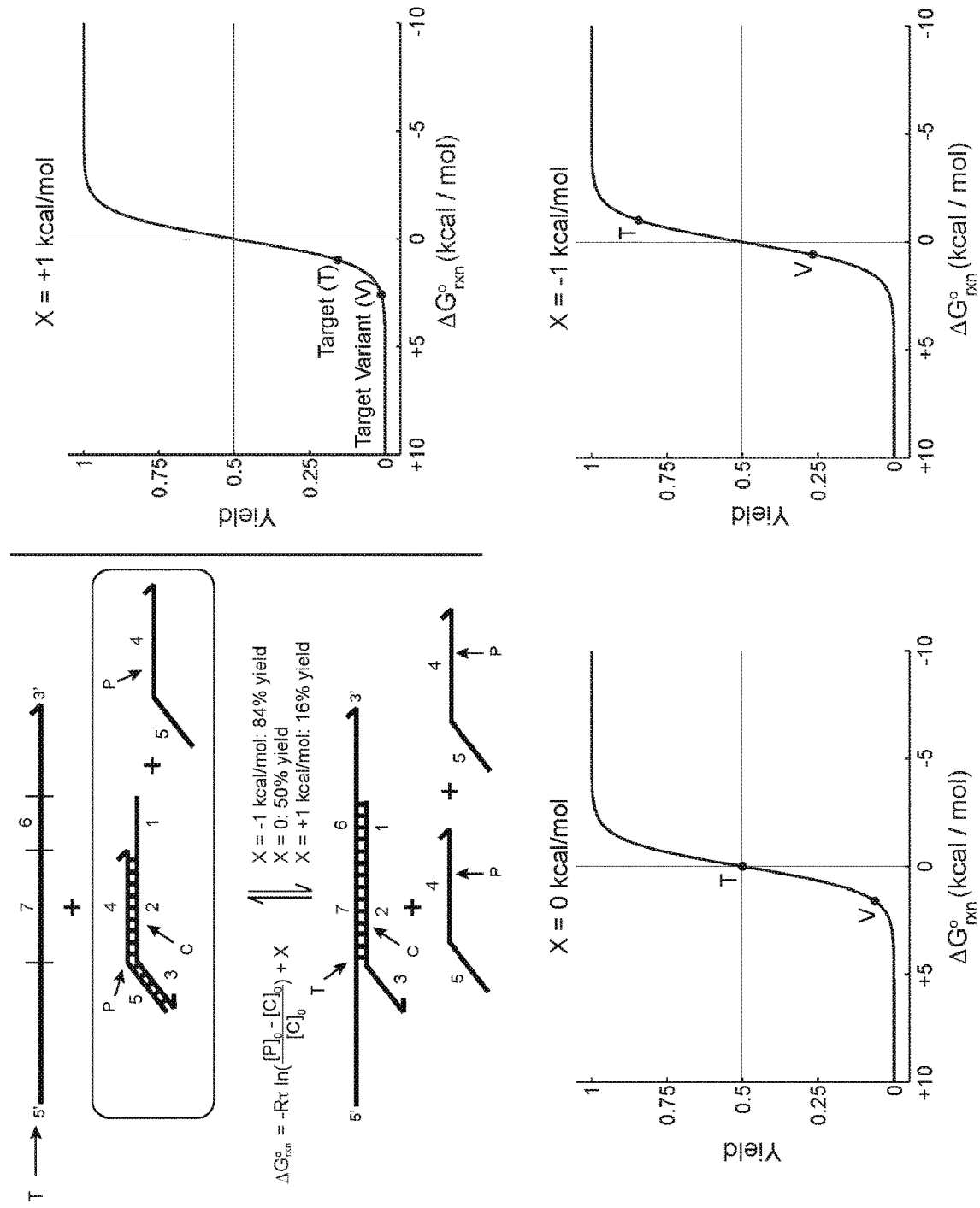

FIG. 8 provides a graphical representation of the different desired yield for target binding, and the tradeoff between specificity and sensitivity. If the reaction standard free energy $\Delta G°_{rxn}$ as determined by Expression 1 (or Expression 3 if a label is used) deviates from (Expression 2 or —Rτ ln(([P]$_0$−[C]$_0$)/[C]$_0$)]) by free energy deviation X, the yield of the target binding will likewise change. For positive values of X, the specificity (against a target variant V) will be improved, but sensitivity (yield) will be reduced. For negative values of X, the sensitivity will be improved, but specificity will be reduced. For particular applications, either specificity or sensitivity may be more important, and the ability to fine-tune thermodynamics via methods presented herein improves upon the prior art.

Figure 9:
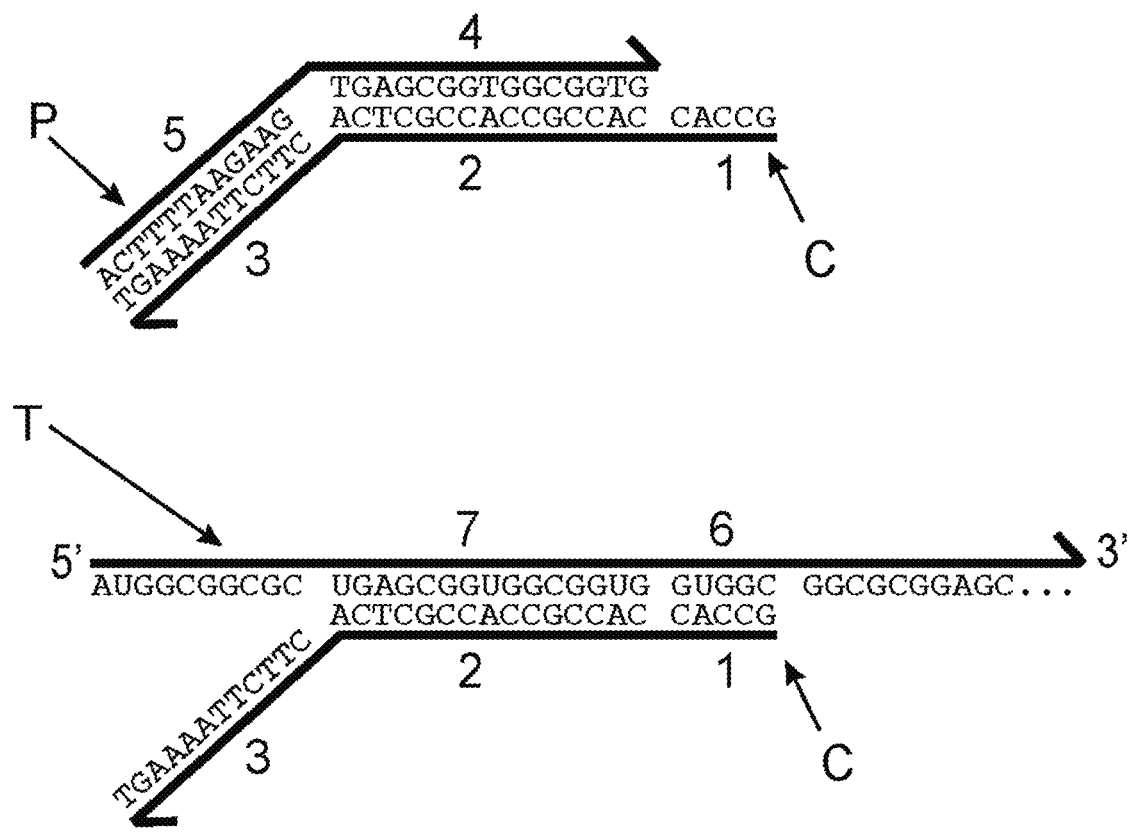

FIG. 9 provides an exemplary probe of the present disclosure (Example 1; the Protector has a sequence according to SEQ ID NO: 3, the Complement has a sequence according to SEQ ID NO: 4, and the Target has a sequence according to SEQ ID NO: 5) targeting a BRAF expressed mRNA subsequence at nucleotides 11-30 at τ=37° C., [Na$^+$]=1M. Based on literature parameters, $\Delta G°_{rxn}$ is calculated to be +0.15 kcal/mol and ([P]$_0$−[C]$_0$/[C]$_0$=0.78 is recommended to achieve X=0. At ([P]$_0$−[C]$_0$)/[C]$_0$=7.8, X is +1.42 kcal/mol, and at ([P]$_0$−[C]$_0$)/[C]$_0$=0.10, X is −1.27 kcal/mol.

Figure 10:
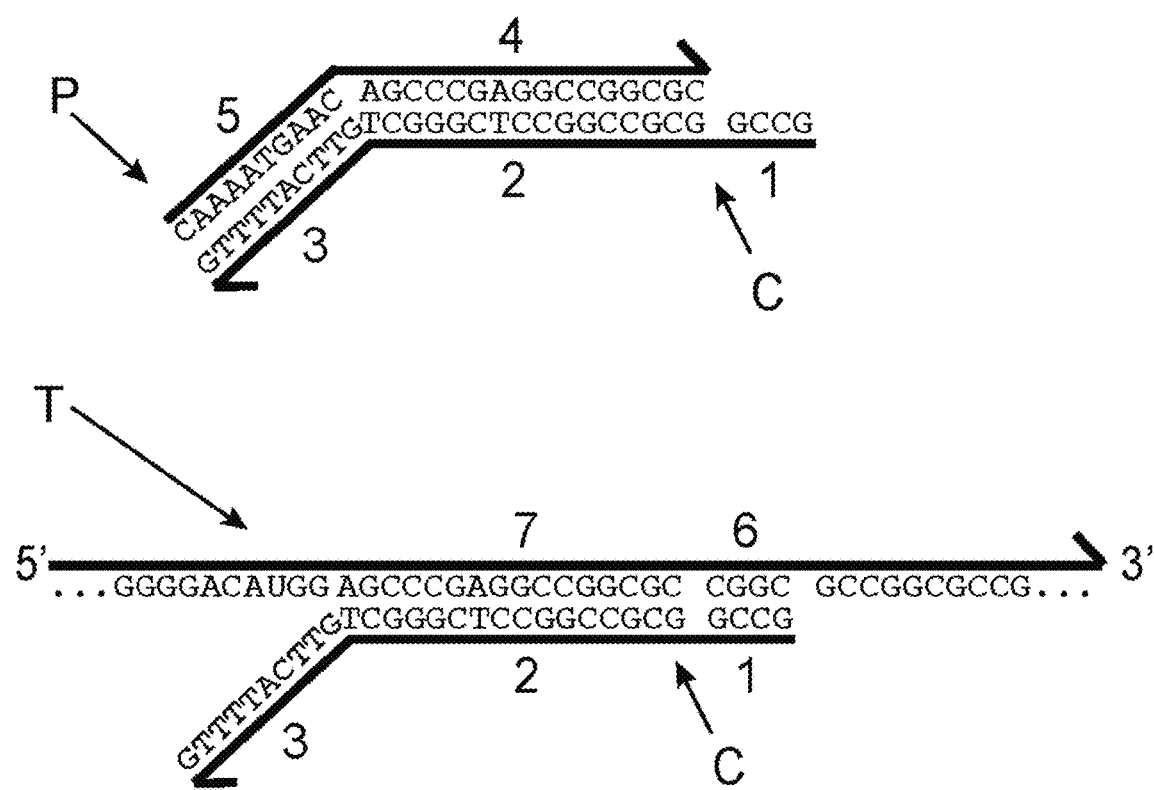

FIG. 10 provides an exemplary probe of the present disclosure (Example 2; the Protector has a sequence according to SEQ ID NO: 6, the Complement has a sequence according to SEQ ID NO: 7, and the Target has a sequence according to SEQ ID NO: 8) targeting a BRAF expressed mRNA subsequence at nucleotides 71-90 at τ=37° C., [Na$^+$]=1M. Based on literature parameters, $\Delta G°_{rxn}$ is calculated to be −0.61 kcal/mol and ([P]$_0$−[C]$_0$)/[C]$_0$=2.69 is recommended to achieve X=0.

Figure 11:
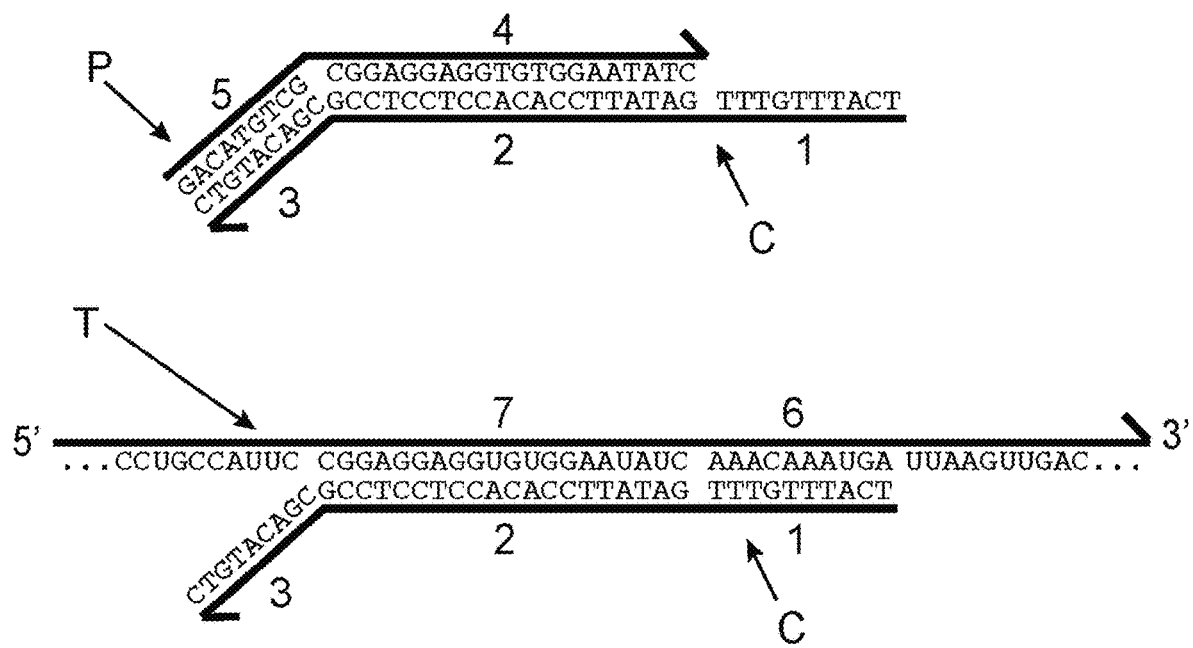

FIG. 11 provides an exemplary probe of the present disclosure (Example 3; the Protector has a sequence according to SEQ ID NO: 9, the Complement has a sequence according to SEQ ID NO: 10, and the Target has a sequence according to SEQ ID NO: 11) targeting a BRAF expressed mRNA subsequence at nucleotides 131-160 at τ=37° C., [Na$^+$]=1M. Based on literature parameters, $\Delta G°_{rxn}$ is calculated to be −1.54 kcal/mol and ([P]$_0$−[C]$_0$)/[C]$_0$=12.14 is recommended to achieve X=0.

Figure 12:
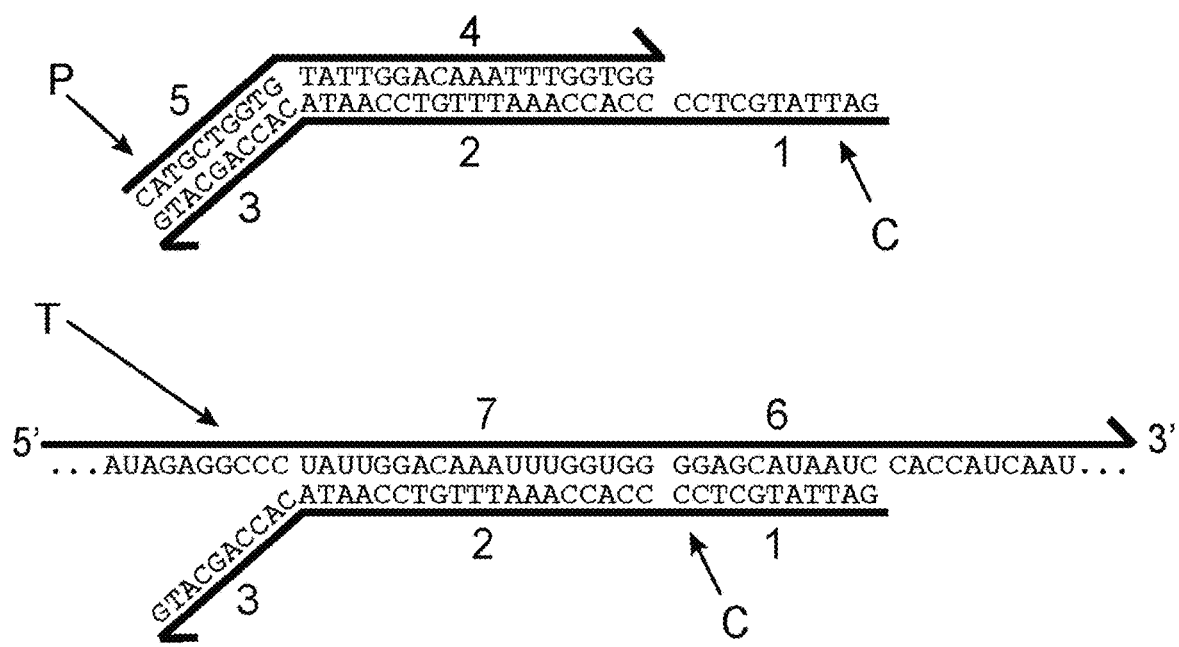

FIG. 12 provides an exemplary probe of the present disclosure (Example 4; the Protector has a sequence according to SEQ ID NO: 12, the Complement has a sequence according to SEQ ID NO: 13, and the Target has a sequence according to SEQ ID NO: 14) targeting a BRAF expressed mRNA subsequence at nucleotides 191-220 at τ=52° C., [Na$^+$]=1M. Based on literature parameters, $\Delta G°_{rxn}$ is calculated to be −0.46 kcal/mol and ([P]$_o$−[C]$_0$)/[C]$_0$=2.11 is recommended to achieve X=0.

Figure 13:
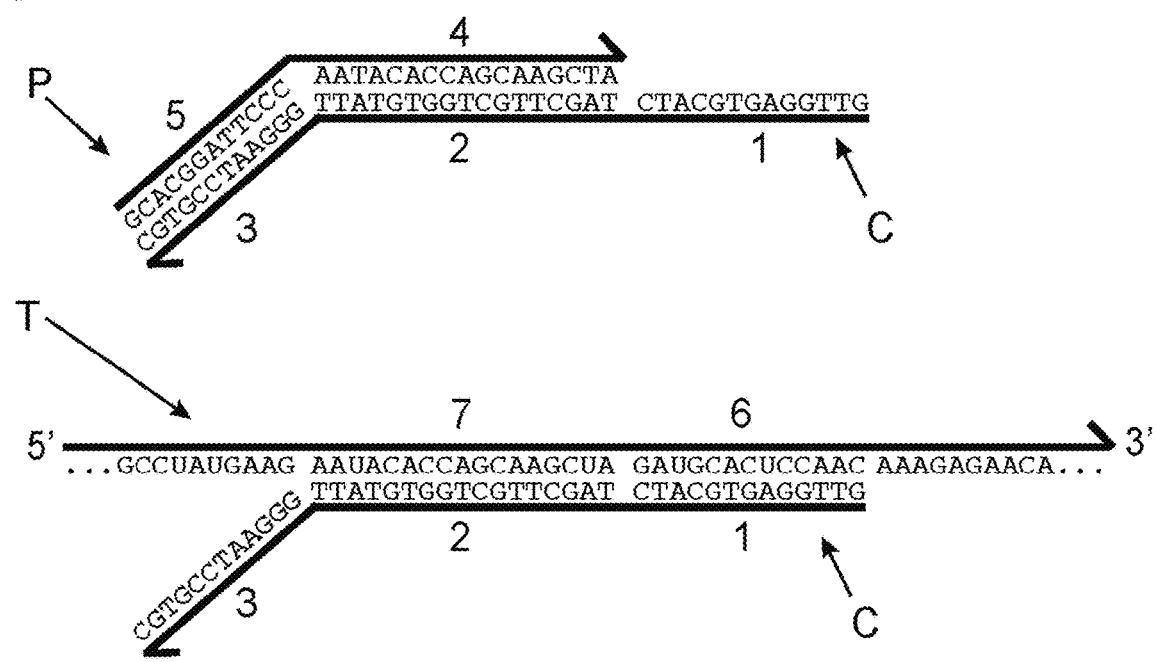

FIG. 13 provides an exemplary probe of the present disclosure (Example 5; the Protector has a sequence according to SEQ ID NO: 15, the Complement has a sequence according to SEQ ID NO: 16, and the Target has a sequence according to SEQ ID NO: 17) targeting a BRAF expressed mRNA subsequence at nucleotides 251-280 at τ=65° C., [Na$^+$]=1M. Based on literature parameters, $\Delta G°_{rxn}$ is calculated to be −1.49 kcal/mol and ([P]$_0$−[C]$_0$)/[C]$_0$=11.2 is recommended to achieve X=0.

Figure 14:
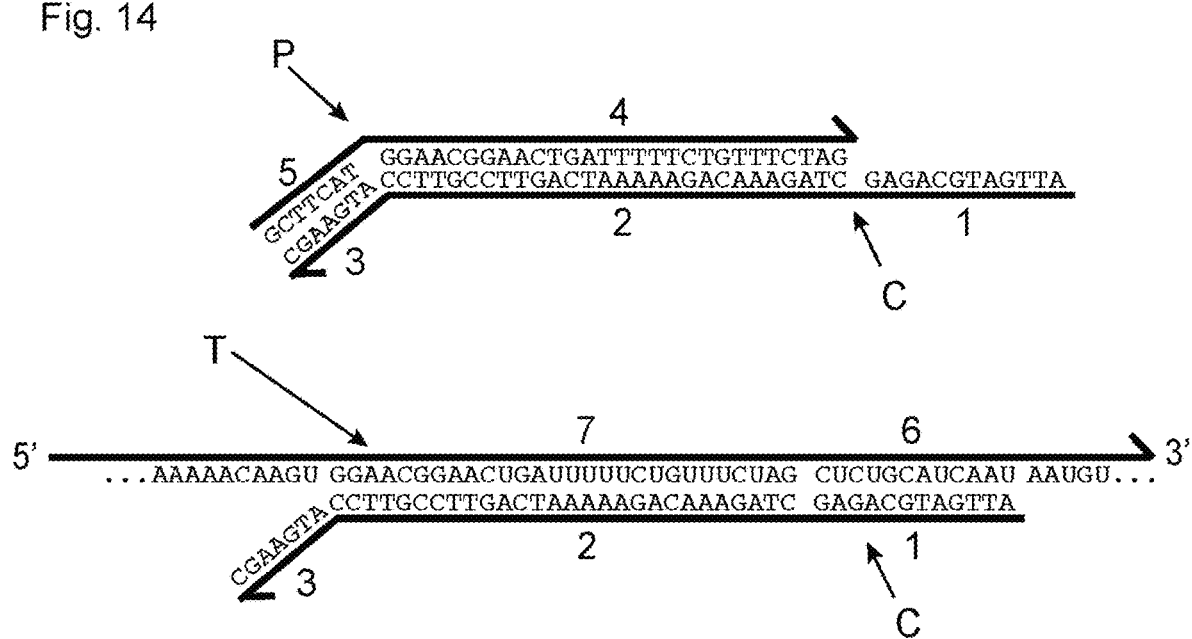

FIG. 14 provides an exemplary probe of the present disclosure (Example 6; the Protector has a sequence according to SEQ ID NO: 18, the Complement has a sequence according to SEQ ID NO: 19, and the Target has a sequence according to SEQ ID NO: 20) targeting a BRAF expressed mRNA subsequence at nucleotides 311-350 at Δ=52° C., [Na$^0$]=1M. Based on literature parameters, $\Delta G°_{rxn}$ is calculated to be −0.22 kcal/mol and ([P]$_0$−[C]$_0$)/[C]$_0$=1.43 is recommended to achieve X=0.

Figure 15:
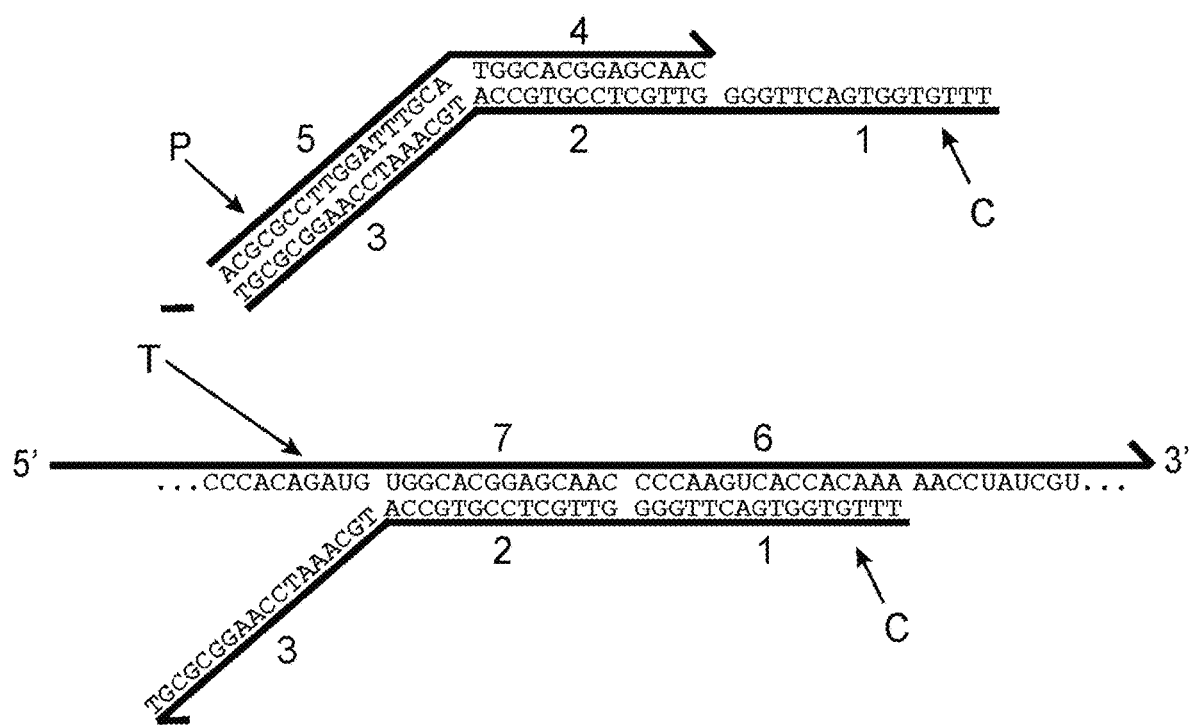

FIG. 15 provides an exemplary probe of the present disclosure (Example 7; the Protector has a sequence according to SEQ ID NO: 21, the Complement has a sequence according to SEQ ID NO: 22, and the Target has a sequence according to SEQ ID NO: 23) targeting a BRAF expressed mRNA subsequence at nucleotides 431-460 at $\Delta$=65° C., [Na$^+$]=1M. Based on literature parameters, $\Delta G°_{rxn}$ is calculated to be +1.03 kcal/mol and ([P]$_0$-[C]$_0$)/[C]$_0$=0.19 is recommended to achieve X=0.

Figure 16:
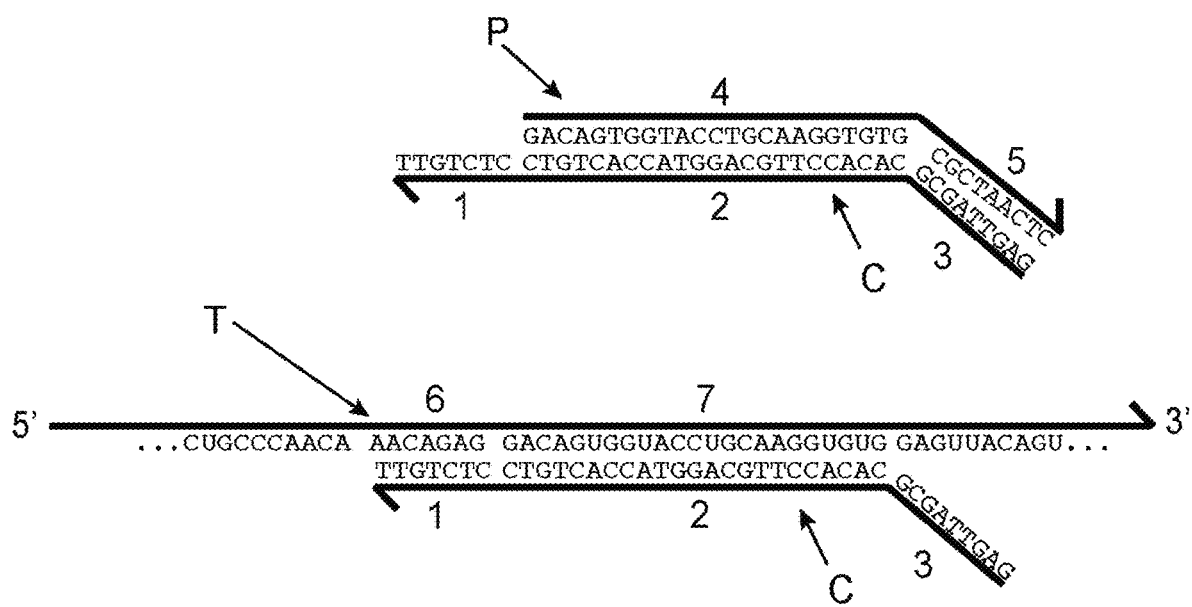

FIG. 16 provides an exemplary probe of the present disclosure (Example 8; the Protector has a sequence according to SEQ ID NO: 24, the Complement has a sequence according to SEQ ID NO: 25, and the Target has a sequence according to SEQ ID NO: 26) with an alternative orientation targeting a BRAF expressed mRNA subsequence at nucleotides 491-520 at $\tau$=37° C., [Na$^+$]=1M. Based on literature parameters, $\Delta G°_{rxn}$ is calculated to be −0.27 kcal/mol and ([P]$_0$-[C]$_0$)/[C]$_0$=1.55 is recommended to achieve X=0.

Figure 17:
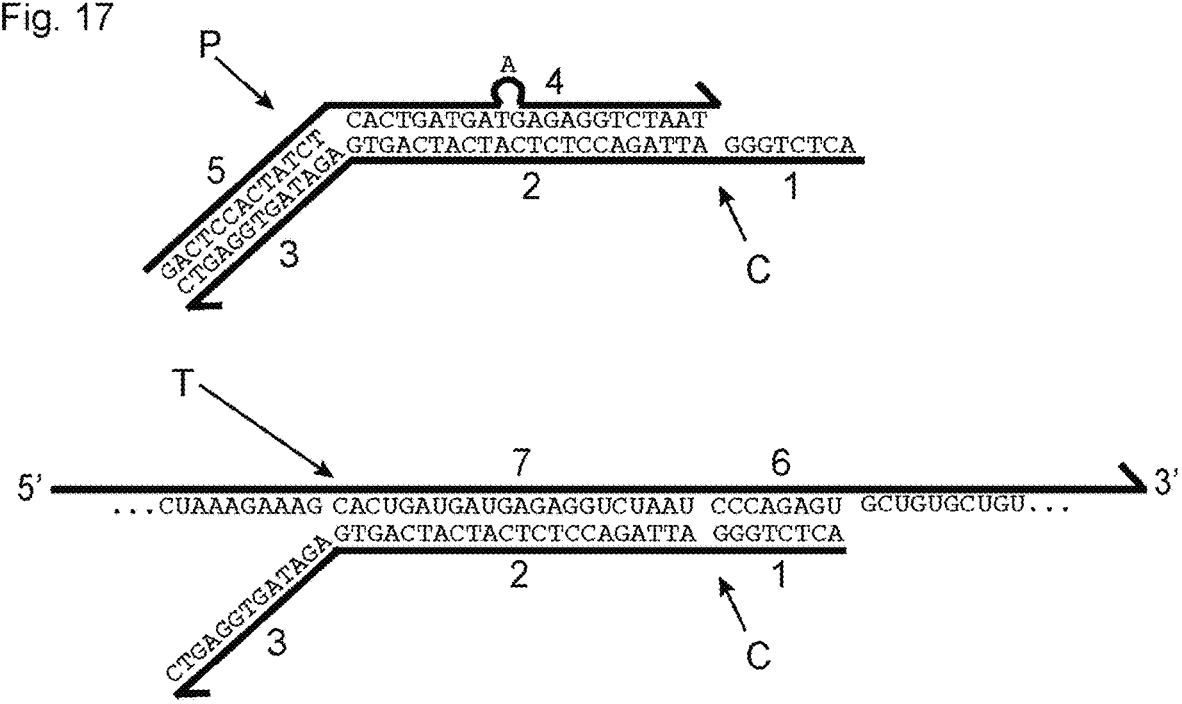

FIG. 17 provides an exemplary probe of the present disclosure (Example 9; the Protector has a sequence according to SEQ ID NO: 27, the Complement has a sequence according to SEQ ID NO: 28, and the Target has a sequence according to SEQ ID NO: 29) with an intentional single nucleotide mismatch in the target-homologous-region (the fourth region) of the protector strand targeting a BRAF expressed mRNA subsequence at nucleotides 551-580 at $\tau$=37° C., [Na$^+$]=1M. Based on literature parameters, $\Delta G°_{rxn}$ is calculated to be −0.37 kcal/mol and ([P]$_0$-[C]$_0$)/[C]$_0$=1.82 is recommended to achieve X=0.

Figure 18:
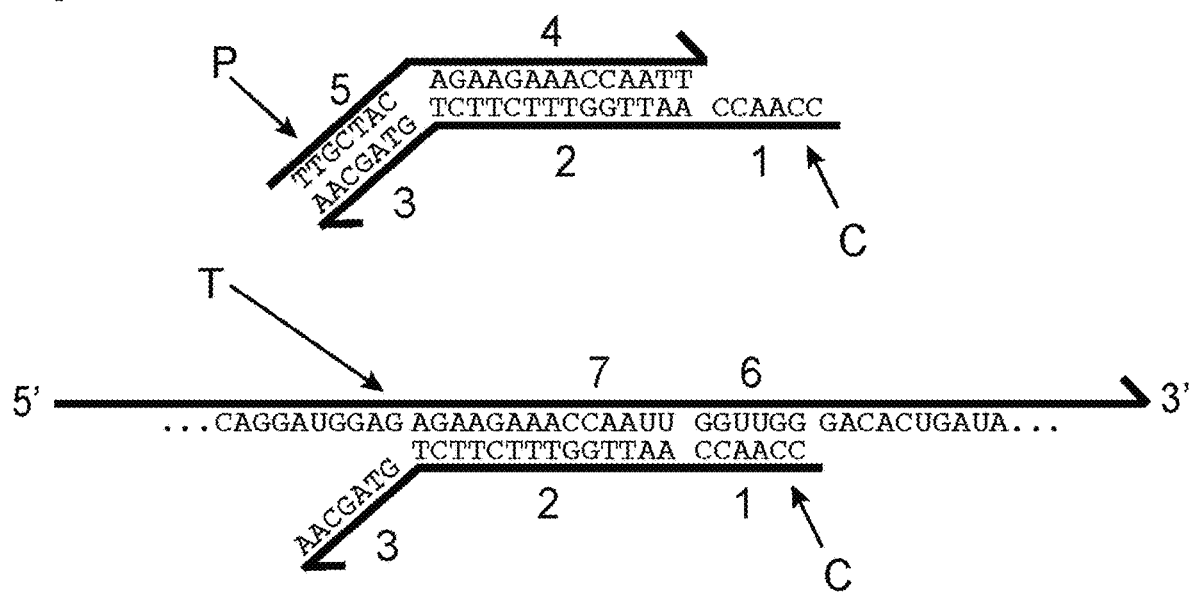

FIG. 18 provides an exemplary probe of the present disclosure (Example 10; the Protector has a sequence according to SEQ ID NO: 30, the Complement has a sequence according to SEQ ID NO: 31, and the Target has a sequence according to SEQ ID NO: 32) targeting a BRAF expressed mRNA subsequence at nucleotides 611-630 at $\tau$=25° C., [Na$^+$]=1M. Based on literature parameters, $\Delta G°_{rxn}$ is calculated to be −0.66 kcal/mol and ([P]$_0$-[C]$_0$)/[C]$_0$=3.0 is recommended to achieve X=0.

Figure 19:
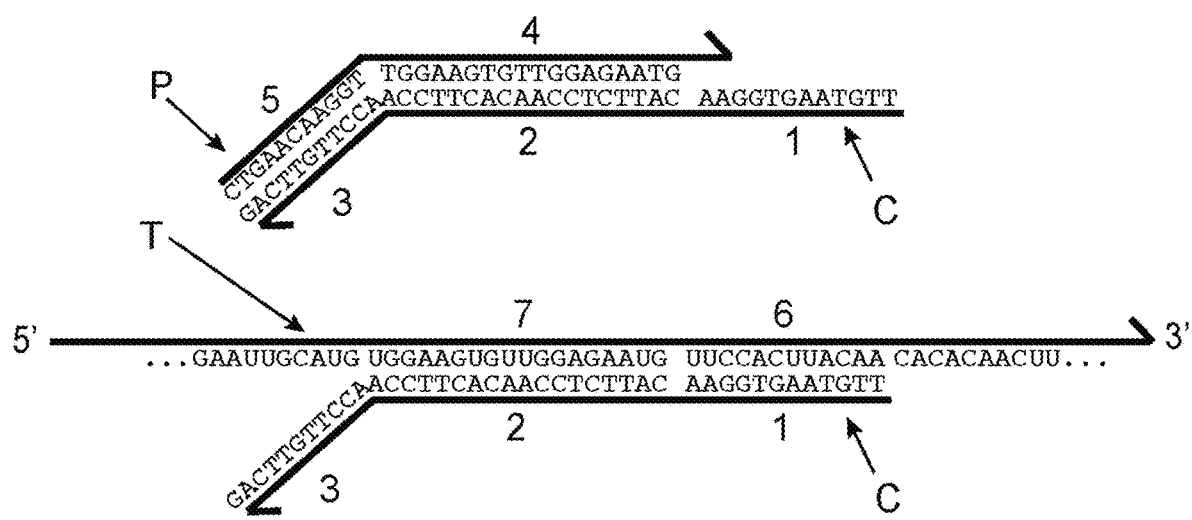

FIG. 19 provides an exemplary probe of the present disclosure (Example 11; the Protector has a sequence according to SEQ ID NO: 33, the Complement has a sequence according to SEQ ID NO: 34, and the Target has a sequence according to SEQ ID NO: 35) targeting a BRAF expressed mRNA subsequence at nucleotides 671-700 at $\tau$=25° C., [Na$^+$]=1M, 30% formamide. Based on literature parameters and an assumption that 1% formamide is equivalent to a temperature increase of 0.6° C., $\Delta G°_{rxn}$ is calculated to be 0.32 kcal/mol and ([P]$_0$-[C]$_0$)/[C]$_0$=0.58 is recommended to achieve X=0.

Figure 20:
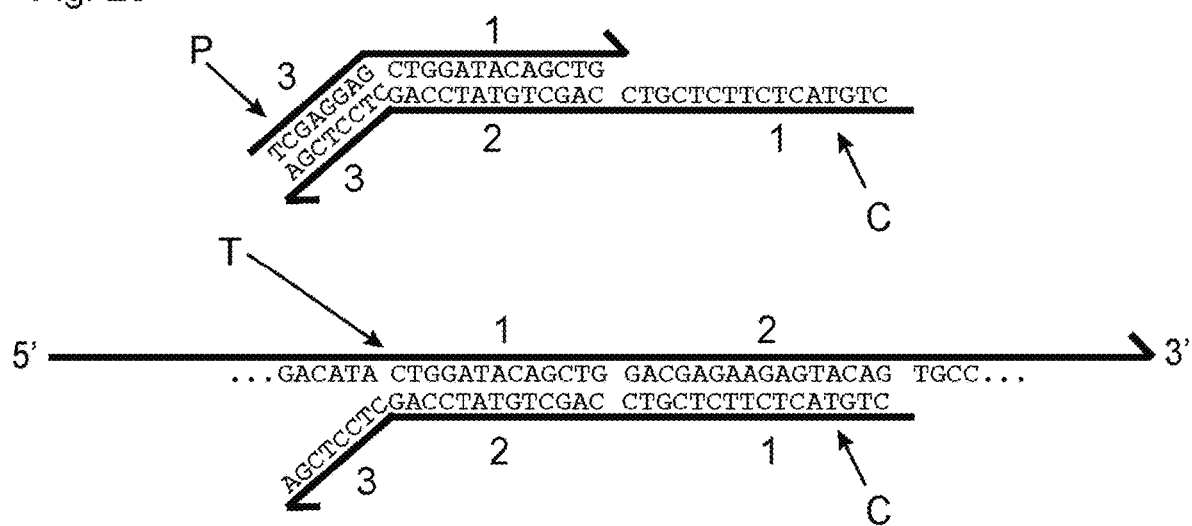

FIG. 20 provides an exemplary probe of the present disclosure (Example 12; the Protector has a sequence according to SEQ ID NO: 36, the Complement has a sequence according to SEQ ID NO: 37, and the Target has a sequence according to SEQ ID NO: 38) targeting a DNA sequence at nucleotides 671-700 at $\tau$=62° C., [Mg$^{2+}$]=3 mM. Based on literature parameters, $\Delta G°_{rxn}$ is calculated to be −3.07 kcal/mol and ([P]$_0$-[C]$_0$)/[C]$_0$=100 is recommended to achieve X=0.

Figure 21:
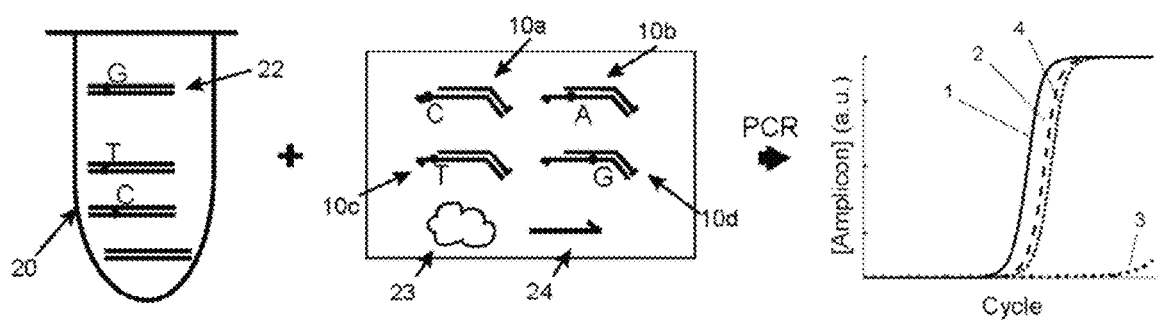

FIG. 21 provides a schematic overview of hotspot multiplexing PCR using probes of the present disclosure as primers. A sample 20 that comprises desired target nucleic acid molecules 22 is mixed with enzyme 23, a forward primer 24, and a reverser primer set 10a-10d. The target nucleic acid molecules 22 comprise single-base mutations residing at loci close to one another (a "hotspot"), and are typically challenging to detect via standard PCR primers. Due to the fact that the present probes possess selectivity to single nucleotide mismatches along the entire length of the primer, the present probes may be uniquely advantageous in hotspot multiplexed PCR primers. Additionally, the use of the present probes as PCR primers, being primarily double-stranded, will suppress the formation of primer dimers, which often limits multiplexed amplification capabilities for PCR. By using different fluorescence channels (1, 2, 3, and 4), each target could be quantitated with very little undesired cross-interaction.

Figure 22:
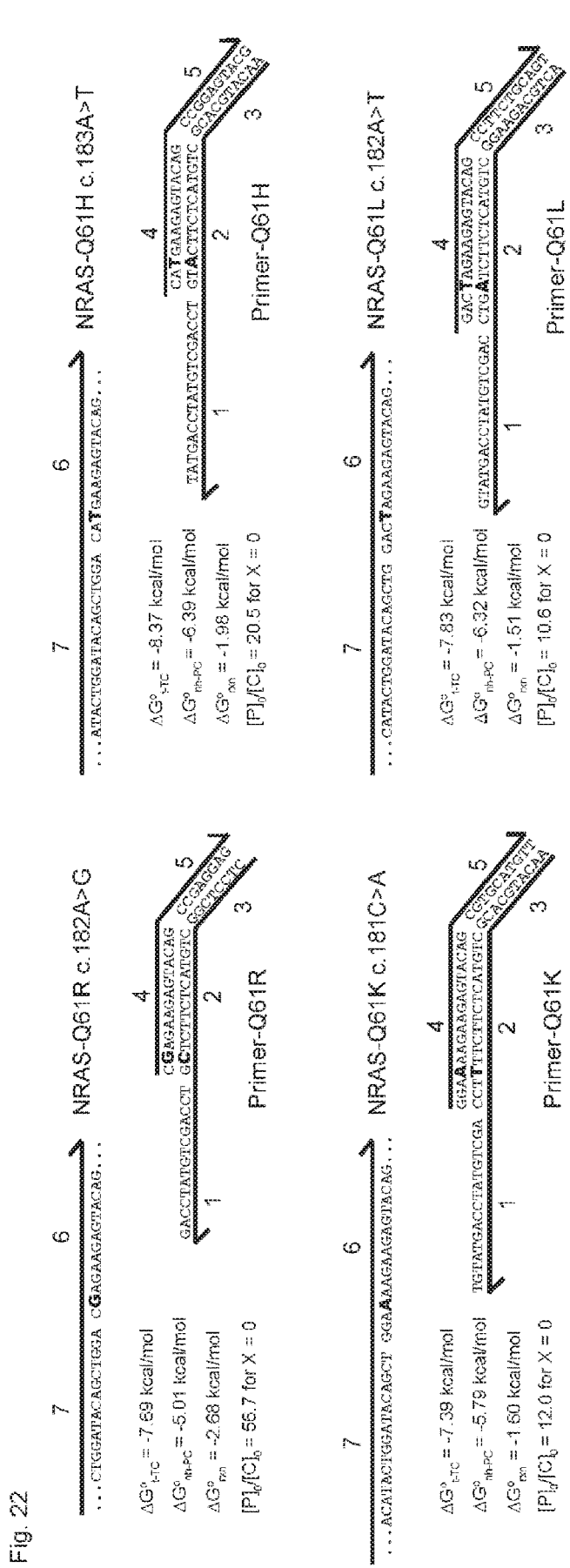

FIG. 22 provides an exemplary hotspot multiplexing PCR reverse primer set using probes of the present disclosure targeting four various NRAS codon 61 mutations. Sequence design and energy calculations are based on the descriptions of design above, and the [P]$_0$/[C]$_0$ ratio that theoretically achieves X =0 are calculated for each primer system. For NRAS-Q61R c. 182A>G, the Protector has a sequence according to SEQ ID NO: 40, the Complement has a sequence according to SEQ ID NO: 41, and the Target has a sequence according to SEQ ID NO: 39. For NRAS-Q61H c. 183A>T, the Protector has a sequence according to SEQ ID NO: 43, the Complement has a sequence according to SEQ ID NO: 44, and the Target has a sequence according to SEQ ID NO: 42. For NRAS-Q61K c. 181C>A, the Protector has a sequence according to SEQ ID NO: 46, the Complement has a sequence according to SEQ ID NO: 44, and the Target has a sequence according to SEQ ID NO: 47. For NRAS-Q61L c. 182A>T, the Protector has a sequence according to SEQ ID NO: 49, the Complement has a sequence according to SEQ ID NO: 50, and the Target has a sequence according to SEQ ID NO: 48.

Figure 23:
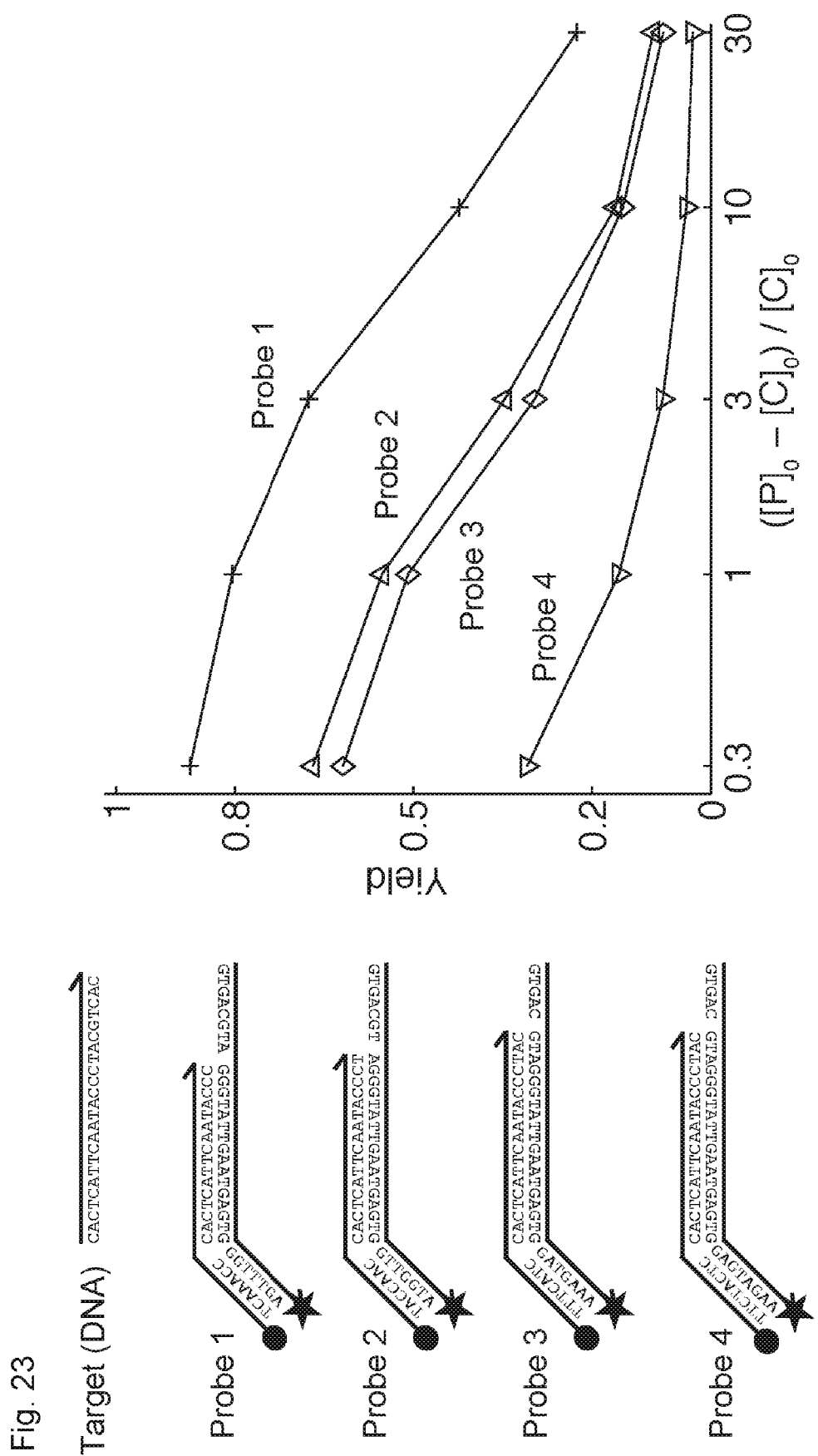

FIG. 23 provides fine-tuning of probes directed to a DNA target by modifying the [P]$_0$/[C]$_0$ ratio. Probes in this figure were designed to bind to the same DNA target with different reaction standard free energies. Each complement strand was modified by a TAMRA fluorophore at 3' end while each protector strand by an Iowa Black RQ quencher at 5' end. Hybridization yields were experimentally obtained at different an ([C]$_0$)/[C]$_0$ ratios via fluorescence. The results indicate that each probe shown in this figure is tunable in specificity and sensitivity. All experiments were done with 1X PBS at 25° C. The Target has a sequence according to SEQ ID NO: 51. Probe 1 has a Protector sequence according to SEQ ID NO: 52 and a Complement sequence according to SEQ ID NO: 53. Probe 2 has a Protector sequence according to SEQ ID NO: 54 and a Complement sequence according to SEQ ID NO: 55. Probe 3 has a Protector sequence according to SEQ ID NO: 56 and a Complement sequence according to SEQ ID NO: 57. Probe 4 has a Protector sequence according to SEQ ID NO: 58 and a Complement sequence according to SEQ ID NO: 59.

Figure 24:
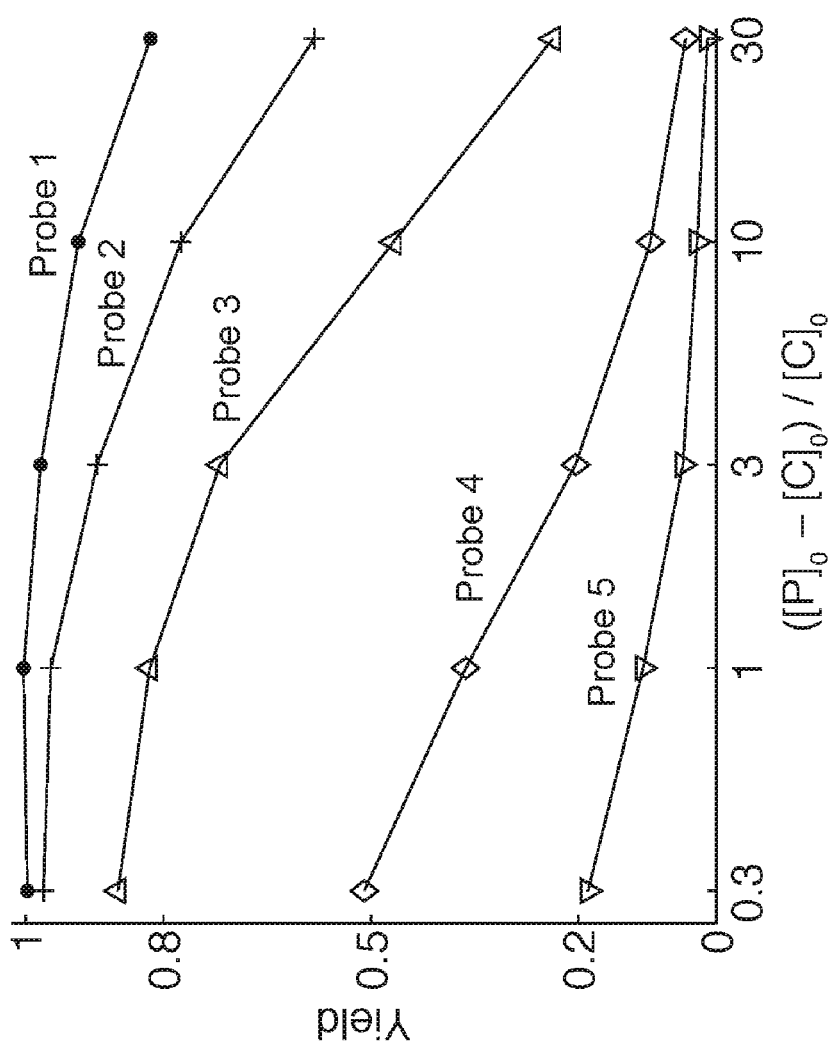
Figure 24:
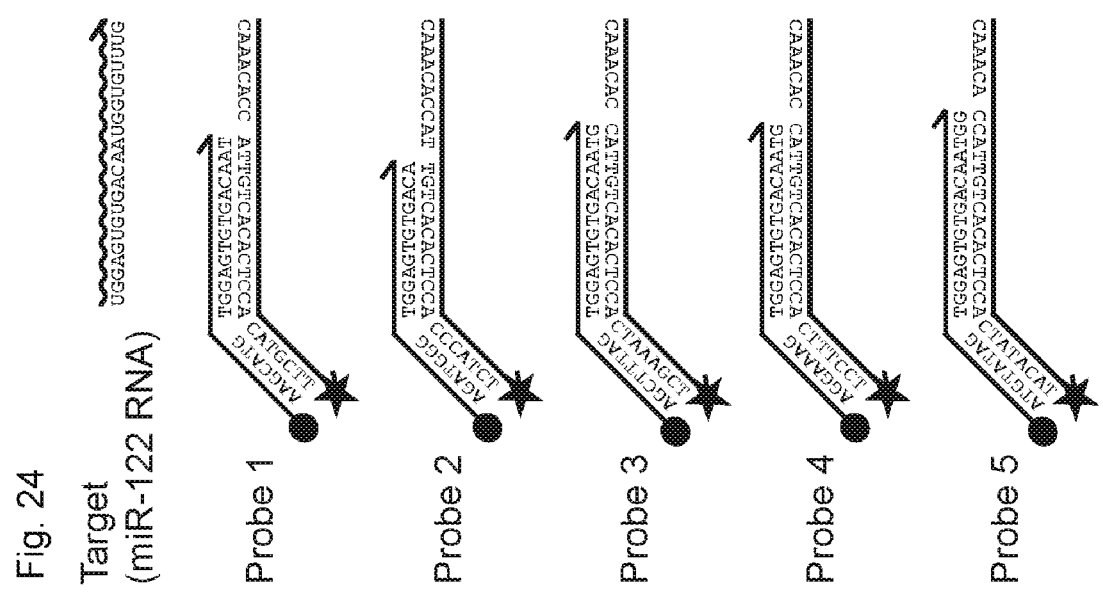

FIG. 24 provides fine-tuning of probes targeting an RNA sequence (synthetic miR-122) by modifying the [P]$_0$/[C]$_0$ ratio. The probe design process was similar to that of FIG. 22, except that RNA-DNA binding parameters were used. Experimental procedures were the same as DNA target. The results show that the sensitivity/specificity tradeoff of probes for RNA target are also adjustable. The Target has a sequence according to SEQ ID NO: 60. Probe 1 has a Protector sequence according to SEQ ID NO: 61 and a Complement sequence according to SEQ ID NO: 62. Probe 2 has a Protector sequence according to SEQ ID NO: 63 and a Complement sequence according to SEQ ID NO: 64. Probe 3 has a Protector sequence according to SEQ ID NO: 65 and a Complement sequence according to SEQ ID NO: 66. Probe 4 has a Protector sequence according to SEQ ID NO: 67 and a Complement sequence according to SEQ ID NO: 68. Probe 5 has a Protector sequence according to SEQ ID NO: 69 and a Complement sequence according to SEQ ID NO: 70.

Figure 25:
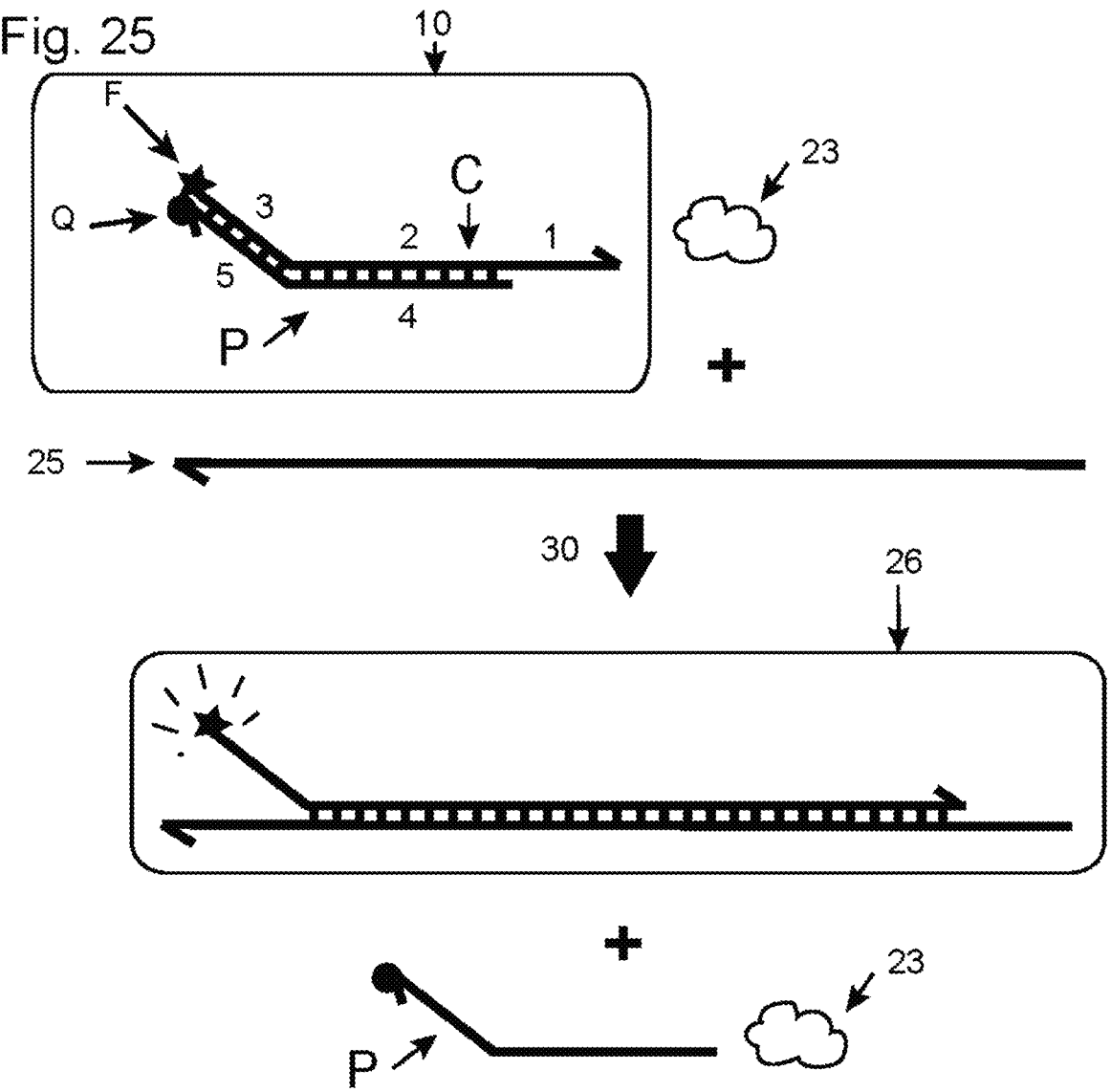

FIG. 25 provides a schematic overview of selectively amplifying a target nucleic acid molecule using probes of the present disclosure as self-reporting primers. The first nucleic acid strand of the primer 10 comprises a fluorophore F on one end, and the second nucleic acid strand of the primer comprises a quencher Q on the other end. During amplification process 30, upon hybridization to the desired target nucleic acid molecule 25, fluorescence signal increases as the second nucleic acid strand of the primer P diffuses away, indicating the formation of amplicon 26.

Figure 26:
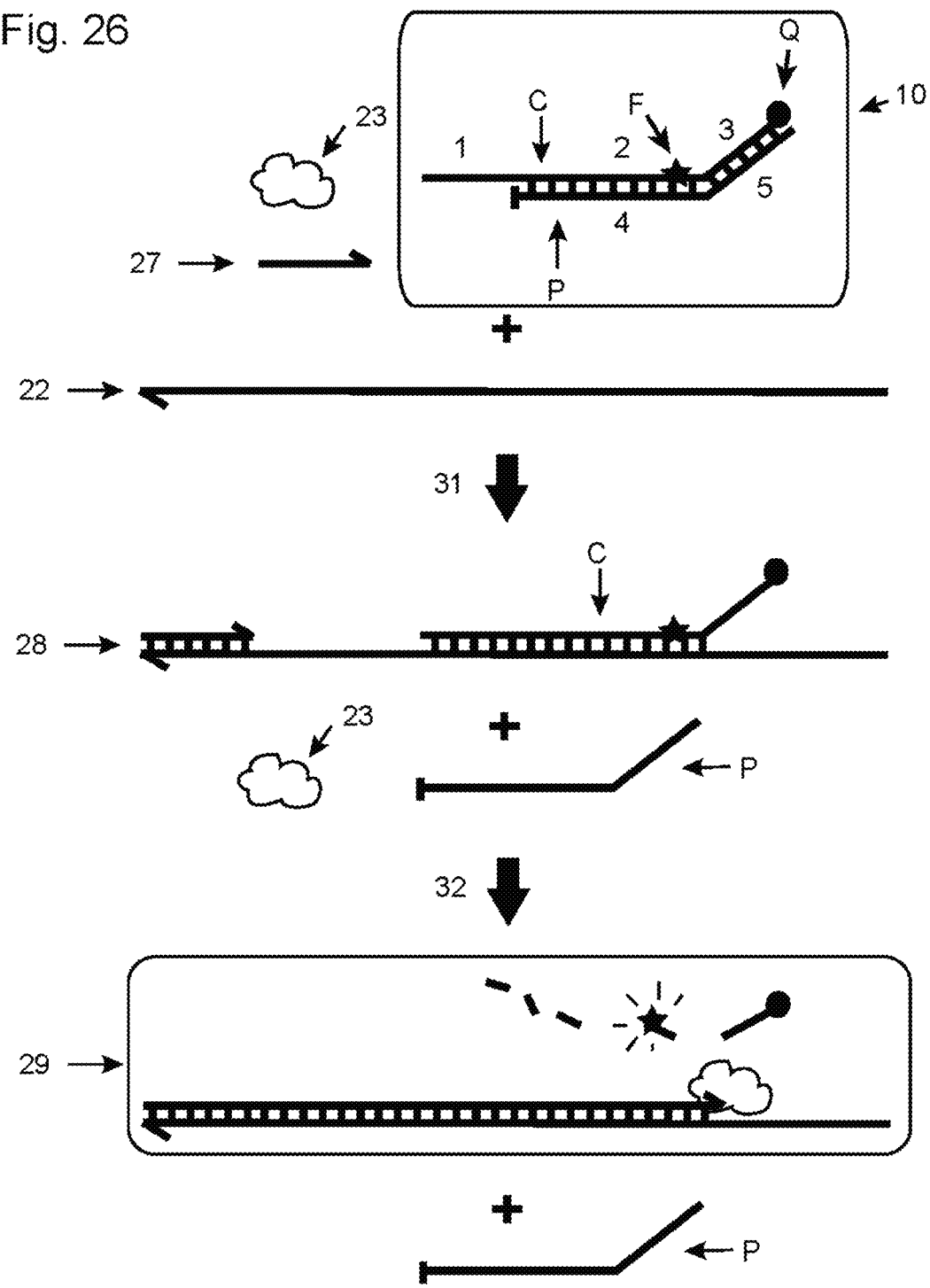

FIG. 26 provides a schematic overview of amplifying a target nucleic acid molecule using probes of the present disclosure as fluorophore-labeled probes to quantitate the amount of desired amplicons formed through the amplification. A sample that possibly comprises desired target nucleic acid molecule 22 is mixed with enzyme 23, forward primer 27, reverse primer (not shown), and fluorophore-labeled probe 10. The first nucleic acid strand of the probe C is functionalized with a fluorophore F internally and a quencher at the 3' end, so that the probe is natively dark due to the close proximity of the fluorophore and quencher. The forward primer and the first nucleic acid strand of the probe C hybridize to the desired target nucleotide molecule during the annealing process 31, while the second nucleic acid strand is displaced by the target nucleic acid molecule. During the extension process 32, enzyme 23 with exonuclease activity extends the primer and cleaves the phosphodiester bonds of first nucleic acid strand, resulting the increase of fluorescence signal.

While the present disclosure is susceptible to various modifications and alternative forms, specific example instances have been shown in the figures and are herein described in more detail. It should be understood, however, that the description of specific example instances is not intended to limit the invention to the particular forms disclosed, but on the contrary, this disclosure is to cover all modifications and equivalents as illustrated, in part, by the appended claims.

DESCRIPTION

The nucleic acid probe systems described herein possess provide several advantages over previously described system. First, the methods and compositions described herein provide for more economical DNA probes to assay RNA targets of specific sequence; DNA probes to RNA targets may also exhibit improved specificity because RNA hybridization is generally less specific than DNA hybridization. Additionally, the methods and compositions here allow modified nucleic acid probes, such as those incorporating 2'-O-methyl nucleotides or locked nucleic acid (LNA), to benefit from robust single nucleotide specificity; these modified nucleic acid probes may possess desirable properties such as nuclease resistance. Second, the methods and compositions described herein provide specificity and sensitivity performance which can be finely tuned by modification of the relative concentrations of protector and complement in the probe system. Additionally, the probe systems also possess two other desirable features: the probes described herein are extremely specific and the probes described herein are operable across a wide range of temperature and salt concentrations and are therefore functionally reliable under many different experimental conditions. For example, a single-base change results in binding yields that differ by approximately 30-fold across temperatures from 10° C. to 70° C. Finally, the probes described herein are kinetically fast. For example, the probe of the present disclosure interacts with the target nucleic acid molecule within a factor of 10 of hybridization.

An overview of probe system 10 consistent with the present disclosure reacting with its intended target T is shown in FIGS. 2A and B. In this example, probe system 10 consists of a protector oligonucleotide/strand P and a complement oligonucleotide/strand C with the protector P existing in excess of the complement C. Protector P and complement C can hybridize to form a partially double-stranded complex; this is true regardless of whether protector P and complement C are introduced separately to target T, or pre-reacted to form the complex. Additionally, in some instances, there may be an excess of complement C or protector P such that the excess strand may exist as a single stranded molecule in addition to the partially double stranded complex of protector and complement. In FIG. 2A, the concentration ratio $[P]_0/[C]_0$ is selected so that the reaction between target T and probe system 10 has a reaction standard free energy ($\Delta G°_{rxn}$) equal to $(-R\tau \ln(([P]_0-[C]_0)/[C]_0]))$. This results, in some instance, in half of all target molecules T in a sample bound to complement strand C at equilibrium. Referring now to FIG. 2B, a target variant V that differs in sequence from target T in the target-validation 7 or target-toehold 6 regions, potentially by a single base, will bind with more a positive standard free energy ($\Delta G°_V$) and possess significantly lower equilibrium yield (e.g. 2%).

The sequences of protector strand P and complementary strand C are designed based on the sequence of intended target T. Each strand is conceptually divided into a number of non-overlapping regions, as shown in FIG. 1. It is important to note that target-validation region 7 (also referred to herein as the "seventh region") and target-homologous region 4 (also referred to herein as the "fourth region"), while both are partially or fully complementary to target-homologous-complementary region 2 (also referred to herein as the "second region"), can possess different sequences. For example, an RNA target will have a target-validation region 7 containing uracil whereas a DNA protector P will comprise thymine in target-homologous region 4. As another example, region 4 may be partially mismatched to region 2 at certain positions, whereas region 7 is perfectly matched to region 2. As another example, both region 4 and region 7 may be partially mismatched to region 2, but at different nucleotide bases.

The reaction standard free energy for the probe system without a label is provided by $\Delta G°_{rxn} = \Delta G°_{t-TC} - \Delta G°_{nh-PC} + (\Delta G°_{v-TC} - \Delta G°_{h-PC})$ which is also referred to herein and in the appended claims as "Expression 1." The reaction standard free energy for the probe system with a functionalized group or label is provided by $\Delta G°_{rxn} = \Delta G°_{t-TC} - \Delta G°_{nh-PC} + (\Delta G°_{v-TC} - \Delta G°_{h-PC}) + \Delta G°_{label}$ which is referred to herein and in the appended claims as "Expression 3." It should be understood that all standard free energy terms used herein are evaluated at the temperature and buffer conditions at which the composition is applied to the target nucleic acid molecule.

As shown in FIGS. 3 and 5, Expressions 1 and 3 are comprised of a number of components representing the standard free energy of hybridization between the various regions of the protector/complementary/target nucleic acid strands. As depicted therein, the $\Delta G°_{t-TC}$ term represents the standard free energy of hybridization between target-toehold region 6 of target nucleic acid T and target-toehold complementary region 1 of complement strand C of probe system 10. These regions can be either partially complementary or fully complementary. In this instance, the term "partially complementary" is defined as having over 60% of the nucleotides in the first region being complementary to the aligned nucleotides of the sixth region. However, it should be understood that the term "partially complementary" with respect to other paired sequences may have a different meaning.

The $\Delta G°_{nh-PC}$ term represents the standard free energy of hybridization between target-nonhomologous region 5 of protector strand P and target-nonhomologous-complementary region 3 of complement strand C. These regions can be either partially complementary or fully complementary. In this instance, the term "partially complementary" is defined as having over 60% of the nucleotides in the third region being complementary to the aligned nucleotides of the fifth region.

The $\Delta G°_{v-TC}$ term represents the standard free energy of hybridization between target-validation region 7 of target nucleic acid T and target-homologous-complementary region 2 of complement strand C. These regions can be either partially complementary or fully complementary. In this instance, the term "partially complementary" is defined as having over 60% of the nucleotides in the second region being complementary to the aligned nucleotides of the seventh region.

The $\Delta G°_{h-PC}$ term represents the standard free energy of hybridization between the target-homologous region 4 of protector strand P and target-homologous-complementary region 2 of complement strand C. These regions can be either partially complementary or fully complementary. In this instance, the term "partially complementary" is defined as having over 60% of the nucleotides in the second region being complementary to the aligned nucleotides of the fourth region.

The term $\Delta G°_{label}$ equals the standard free energy of a label on the complement strand ($\Delta G°_F$) minus the standard free energy of the interaction between the label and the protector, including any other functionalized groups on the protector. In the example in FIG. 5, the label of the protector strand (Q) is a quencher specific to the fluorophore (F) of the complement strand.

Referring still to FIG. 1, in certain instances, the design of probe system sequences is such that (1) there is little to no secondary structure in target-toehold-complementary region 1, and (2) there is little to no binding between the target-upstream region 8 and target-nonhomologous-complementary region 3. Here, "little to no secondary structure" in the target-toehold-complementary region is defined as fewer than 50% of the nucleotides in the region being in double-stranded state in the evaluated minimum free energy structure, as computed in the operational temperature and salinity conditions. Here, "little to no binding" between the target-upstream region and target-nonhomologous-complementary region 3 is defined as fewer than 50% of the nucleotides in the target-nonhomologous-complementary region 3 being in double-stranded state in the evaluated minimum free energy structure, as computed in the operational temperature and salinity conditions.

In addition to the reaction standard free energy ($\Delta G°_{rxn}$) as determined, for example, by Expression 1, the present probe design includes consideration of the relative concentrations of the protector and complement strands of the probe. This permits fine tuning of reactions by modifying the ratio of protector strand to complement strand independently of the probe's sequence design. Thus, in one instance, the design of the present nucleic acid hybridization probe system is based on the following:

$$\Delta G°_{rxn} = \Delta G°_{t-TC} - \Delta G°_{nh-PC} + (\Delta G°_{v-TC} - \Delta G°_{h-PC}) = -R\tau \ln(([P]_0 - [C]_0)/[C]_0) + X$$

or $$\Delta G°_{rxn} = \Delta G°_{t-TC} - \Delta G°_{nh-PC} + (\Delta G°_{v-TC} - \Delta G°_{h-PC}) + \Delta G°_{label} = -R\tau \ln(([P]_0 - [C]_0)/[C]_0) + X$$

where X is a value between −5 kcal/mol and +5 kcal/mol.

The value of X further allows the user to control the tradeoff between high molecular sensitivity and high molecular specificity, with more positive values of X favoring higher specificity.

It should be understood that the values of the $\Delta G°$ terms can only be approximately calculated based on currently available literature values, whereas the claimed probes are described and constrained by real $\Delta G°$ terms. Based on our experimental studies of $\Delta G°$ values, calculations based on currently available parameters and software may differ from real values by up to 3 kcal/mol or 15%, whichever is larger.

In contrast, WO 2012/058488 describes the design of nucleic acid hybridization probes in which the primary design constraint is $\Delta G°_{t-TC} \approx \Delta G°_{nh-PC}$, in the language of the present disclosure, where approximately equal to is defined as within 10% of each other. In one embodiment, the standard free energies $\Delta G°_{t-TC}$ and $\Delta G°_{nh-PC}$ for the probes of the current invention differ by more than 10% because the desired value of X differs significantly from 0. In another embodiment, the standard free energies $\Delta G°_{t-TC}$ and $\Delta G°_{nh-PC}$ for the probes of the current invention differ by more than 10% because ($\Delta G°_{v-TC} - \Delta G°_{h-PC}$) differs significantly from 0. In another embodiment, the standard free energies $\Delta G°_{t-TC}$ and $\Delta G°_{nh-PC}$ for the probes of the current invention differ by more than 10% because $([P]_0 - [C]_0)/[C]_0$ differs significantly from 1. In another embodiment, the standard free energies $\Delta G°_{t-TC}$ and $\Delta G°_{nh-PC}$ for the probes of the current invention differ by more than 10% because $\Delta G°_{label}$ differs significantly from 0.

Thus, the present probe system diverges from the prior art in the consideration of the $\Delta G°_{v-TC}$, $\Delta G°_{h-PC}$, $\Delta G°_{label}$, X, and $$\left( \frac{[P]_0 - [C]_0}{[C]_0} \right)$$

terms. Negligence of the $\Delta G°_{v-TC}$, $\Delta G°_{h-PC}$ terms lead to poor probe design in many settings where the nucleotide sequences of region 4 and region 7 are not identical, negligence of the $\Delta G°_{label}$ term leads to poor probe design when fluorophore or other labels are used, negligence of the X term precludes different tradeoffs between specificity and sensitivity, and negligence of the stoichiometric ratio term precludes fine-tuning of probe system behavior independent of sequence design and furthermore cause probes to perform poorly in certain stoichiometries of P and C. Each of these will be discussed in more detail below.

First, referring back to FIG. 2A, the target-validation region 7 of the target T and target-homologous region 4 of protector P may differ in sequence and thermodynamic properties for a number of reasons, importantly in instances where T and P are different types of nucleic acids. For example, target T may be an RNA molecule due to scientific/clinical interest, whereas protector P may be a DNA molecule due to economics/synthesis capabilities. As another example, protector P may comprise a modified nucleic acid, such as 2'-O-methyl nucleotides or locked nucleic acid (LNA). As another example, region 4 and region 7 may both be DNA, but differ in nucleotide sequence in order to benefit from increased kinetics or decreased unwanted biological response.

When target-validation region 7 of target T and target-homologous region 4 of protector P differ, then the $\Delta G°_{v-TC}$ and $\Delta G°_{h-PC}$ terms are unequal, and must be considered in the $\Delta G°_{rxn}$ driven probe system design process. The value of $\Delta G°_{v\text{-}TC}-\Delta G°_{h\text{-}PC}$ can deviate significantly from zero. Referring now to FIG. 4, the distribution of these values for 46 different non-overlapping subsequences of the BRAF transcript RNA (each 50 nt long) versus homologous DNA sequences in binding to a DNA complement, using RNA-DNA hybridization thermodynamics values given by Sugimoto et al. [7] and DNA-DNA hybridization thermodynamics values given by SantaLucia and Hicks [8] is shown. As can be seen therein, not only does the value of $\Delta G°_{v\text{-}TC}-\Delta G°_{h\text{-}PC}$ range from −20 kcal/mol to +20 kcal/mol, the values are also temperature dependent. In contrast, even a 1 kcal/mol difference in $\Delta G°_{rxn}$ can lead to significant changes in sensitivity and/or specificity.

The detection of RNA targets T using DNA probes (P and C) is only one application in which $\Delta G°_{v\text{-}TC}-\Delta G°_{h\text{-}PC}$ must be considered. Other variations of the probe system exist where the target-homologous region of protector P differs from the target-validation region of the target T, either because T and P are different types of nucleic acids (RNA, DNA, LNA, PNA, phosphothioate DNA, 2'-methoxy nucleic acids, etc.) or because of small changes in sequence, which will be discussed in further detail herein below.

By ignoring the $\Delta G°_{v\text{-}TC}-\Delta G°_{h\text{-}PC}$ term, it must be assumed that the total value of this term is 0 kcal/mol. This assumption is satisfied only when target-homologous region 4 of protector P is of identical character and sequence as target-validation region 7 of target T, such as for applications of DNA targets using DNA protectors and where region 7 and 4 possess identical nucleotide sequence.

Second, many applications of detection or imaging of nucleic acids utilize labels to help visualize the existence or quantity of target nucleic acids. These labels can be organic fluorophores, metallic nanoparticles, or haptens that recruit antibodies. Frequently, these labels can have significant thermodynamic effects, stabilizing or destabilizing nucleic acid hybridization. Proper design of probe systems that utilize labels should account for the differential standard free energies of labels with the protector and with the target as shown in FIG. 5.

Third, as mentioned above, the relative concentrations of protector P and complement C serve is an important tuning parameter for the present probe system that exists independently of the probe system's sequence design. Given that current understanding of DNA and RNA hybridization thermodynamics and label thermodynamics are imperfect, the ability to modulate the performance of a particular probe system after design and synthesis is vitally important for practical applications involving these probe systems.

To understand the role of the relative concentrations of P and C in tuning the performance of the probe system, the equilibrium of the reaction between the target and the probe system should be considered. The overall chemical reaction can be written as the expression below.

$$T+PC \rightleftharpoons TC+P$$

Typically, the targets (biological DNA or RNA molecules) are much lower in concentration than the probe components P and PC; the higher concentrations of P and PC aid in driving the reaction to equilibrium quickly. One useful metric for judging the reaction's behavior is the yield or sensitivity of the probe system to target T, which can be expressed as $$\left(\frac{[TC]}{[T]+[TC]}\right).$$

When the sensitivity is roughly 50%, that is, when the equilibrium concentration of unbound T is equal to the equilibrium concentration of T bound to C ([T]=[TC]), the fold-change discrimination against a variant target V ([TC]/[VC]) is within a factor of 2 of optimal. The value of the equilibrium constant Keq that enables [T]=[TC] can be analytically solved by the below expression.

$$K_{eq} = \frac{[TC][P]}{[T][PC]}$$
$$= \frac{[P]}{[PC]}$$

The standard free energy of a reaction can be related to the reaction equilibrium constant by the following expression.

$$\Delta G°_{rxn} = -R\tau \ln(K_{eq})$$
$$= -R\tau \ln\left(\frac{[P]}{[PC]}\right)$$
$$= -R\tau \ln\left(\frac{[P]_0 - [C]_0}{[C]_0}\right)$$

In the above equation, $[P]_0$ denotes the initial concentration of the protector and $[C]_0$ denotes the initial concentration of the complement. Because the target concentration [T] is typically much lower than the concentrations of either protector or probe, the equilibrium concentrations of [P] and [PC] can be approximated as $[P]_0-[C]_0$ and $[C]_0$, respectively. The term $$\left(\frac{[P]_0 - [C]_0}{[C]_0}\right)$$

is scale-invariant, and the concentrations used for $[P]_0$ and $[C]_0$ can therefore be either the high stock concentration added to a sample, or the final concentration achieved after dilution by the sample. Note that $[P]_0$ and $[C]_0$ refer to the total concentrations of P and C, including those present in the partially double-stranded PC species. An alternative method of writing this expression is $([P_{free}]_0/[PC]_0)$, where $[P_{free}]_0$ denotes the initial concentration of free P and $[PC]_0$ denotes the initial concentration of PC.

For use in the present probe system, the concentration for $[P]_0$ may be lower than, the same as, or greater than, but is generally greater than the concentration for $[C]_0$. For example, the concentration for $[P]_0$ as can be from about 1.01 times to about 10,000 times that of $[C]_0$, from about 1.1 times to about 1,000 times that of $[C]_0$, or from about 1.2 times to about 100 times that of $[C]_0$ and including any intermediate range between any of the above provided ranges.

In one instance, probe behavior can be tuned to achieve approximately 50% sensitivity by designing the probe system so that the $\Delta G°_{rxn}$ is close to 0, or from about −5 kcal/mol to about +5 kcal/mol, and then adjusting the $[P]_0$ and $[C]_0$ so that $$\Delta G°_{rxn} = -R\tau \ln\left(\frac{[P]_0 - [C]_0}{[C]_0}\right)$$

is satisfied. Importantly, without tuning the probe system via [P]₀ and [C]₀, it becomes practically impossible to obtain 50% sensitivity (or any other desired sensitivity), due to the coarse-grain nature of adjusting $\Delta G°_{rxn}$ via addition or removal of base pairs/stacks.

FIG. 6 demonstrates that a single additional base pair changes the value of $\Delta G°_{rxn}$ by between −0.6 kcal/mol and −2.2 kcal/mol in 37° C., 1M Na⁺.

In the present disclosure, a novel concept of fine-tuning of $\Delta G°_{rxn}$ via the stoichiometric ratio of protector P to complement C is therefore provided. The accuracy of the stoichiometric ratio between P and C is limited only by the accuracy of liquid handling systems (e.g. pipettor accuracy), and can typically be controlled to within 2%. This 2% accuracy of stoichiometry, in turn, results in the same precision of tuning probe performance −Rτ ln(1.02)=−0.012 kcal/mol as resolution in $\Delta G°_{rxn}$. Thus, tuning the thermodynamics via P to C stoichiometry is over a factor of 50 more fine-grained than prior art methods of tuning thermodynamics via additional base pairs (−0.012 kcal/mol vs −0.60 kcal/mol). Tuning of P and C stoichiometry can occur at the design phase, or dynamically as the probe is being iteratively optimized for a particular application.

The experimental results provided in FIGS. 22 and 23 demonstrate the effectiveness of adjusting the ratio ([P]₀-[C]₀)/[C]₀ in order to tune the specificity/sensitivity tradeoff. FIG. 22 depicts the sequence design of four different probes directed to a DNA target, each designed with a different $\Delta G°_{rxn}$ and the observed yield of the DNA target to each probe for different values of ([P]₀-[C]₀)/[C]₀. FIG. 23 depicts the sequence design of five different probes directed to a RNA target, each designed with a different $\Delta G°_{rxn}$ and the observed yield of the RNA target to each probe for different values of ([P]₀-[C]₀)/[C]₀. As taught previously, larger values of ([P]₀-[C]₀)/[C]₀ monotonically decrease the yield of the hybridization between the target and the probe.

In another aspect, the present disclosure provides a probe system in which $$\Delta G°_{rxn} = -R\tau \ln\left(\frac{[P]_0 - [C]_0}{[C]_0}\right)$$

is not satisfied, but instead provides a slight variation where the values are not equal in order to achieve a different tradeoff between specificity and sensitivity. To this end, the thermodynamic property of the present probe system can be expressed by the following:

$$\Delta G°_{rxn} = -R\tau \ln\left(\frac{[P]_0 - [C]_0}{[C]_0}\right) + X$$

where X is the deviation from 0. In one instance, the value of X is from about −5 kcal/mol to about +5 kcal/mol. For positive values of X, the specificity (against a target variant V) will be improved, but sensitivity (yield) will be reduced. For negative values of X, the sensitivity will be improved but specificity will be reduced as demonstrated in FIG. 8. In practice, certain applications (such as those dealing with rare alleles) may require higher specificity at the cost of sensitivity, or vice versa. The present methods to fine-tune thermodynamics are particularly useful for these applications that require intricate control of sensitivity and specificity (see also Variants).

In yet another aspect, the present disclosure provides for minor sequence differences between target-validation and target-homologous regions. The target-validation region (of the target T) and the target-homologous region (of the protector P) are both intended to be complementary to the target-homologous-complementary region (of the complement C). However, there may be cases where it is desirable to have minor sequence modifications in the target-validation and/or in the target-homologous region, so that the target-validation and/or the target-homologous region are only partially complementary to the target-homologous-complementary region. To this end, in the instance that over 60% of the bases in the target-homologous-complementary region are complementary to the target-validation region, and over 60% of the bases in the target-homologous-complementary region are complementary to the target-homologous region, the resulting probes maintain consistency with the principles of probe construction described herein.

In addition, the present disclosure provides a probe system in which the 5' to 3' orientations of the protector and complement are reversed with respect to the positions of the nonhomologous and toehold regions as shown in FIGS. 7A, 7B, and 7C. Modern nucleic acid synthesis occurs from the 3' end to the 5' end, resulting in truncations and deletions being concentrated at the 5' end. Consequently, it is expected that the original orientation shown in FIGS. 1-6 would be desirable because truncations on the protector and the complement will tend to balance each other energetically, maintaining the desired $\Delta G°_{rxn}$. In contrast, in the design orientation shown in FIGS. 7A, 7B, and 7C, truncations in both the protector and the complement will tend to make $\Delta G°_{rxn}$ more negative, reducing the reliability and specificity of the probe system. These effects are mitigated when the protector and complement oligonucleotides are purified post-synthesis, such as by high pressure liquid chromatography (HPLC) or polyacrylamide gel electrophoresis (PAGE).

In the analysis of reaction standard free energy ($\Delta G°_{rxn}$), the standard free energy of formation $\Delta G°$ of an unstructured oligonucleotide is defined to be 0. The equilibrium constant ($K_{eq}$) of the reaction between the target T and the probe system (P and C) can be directly calculated from the reaction's standard free energy $\Delta G°_{rxn}$ via the following expression: $K_{eq} = e^{-\Delta G°_{rxn}/R\tau}$
where R=8.314 J/mol K is the ideal gas constant (alternatively, Boltzmann constant), and τ is the ambient temperature in Kelvin.

In the design of the present probe system, the reaction $\Delta G°_{rxn}$ is broken down into the sum of a number of $\Delta G°$ terms denoting the standard free energy of hybridization of various regions of the complement strand to target strand and complement strand to protector strand (e.g. $\Delta G°_{nh-PC}$ denotes the hybridization of the target-nonhomologous region to the target-nonhomologous-complement region). The values of these terms can be approximately calculated by adding the standard free energies of base stacks as described in more detail herein below, though current literature-provided standard free energy values are incomplete and of limited accuracy. Experimental testing is needed to determine the true values of $\Delta G°_{rxn}$ for each probe, but the literature-guided values provide a rough (typically within 3 kcal/mol or 15%) estimate of the $\Delta G°_{rxn}$.

In one instance, the standard free energies of hybridization between regions of the present probe system are calculated based on a base pair stacking approach. In this method, two adjacent base pairs comprise one stack, which has a defined enthalpy)($\Delta H°$) and entropy)($\Delta S°$) value. The standard free energy of each stack ($\Delta G°$ at a particular temperature T (in Kelvin) can be calculated from the equation $\Delta G°=\Delta H°-\tau \Delta S°$. The standard free energies of several stacks can be summed to evaluate the standard free energy of a binding region. For example, the standard free energy of a 'CTC' region pairing to a 'GAG' region is the standard free energy of stack 'CT/GA' plus the standard free energy of stack 'TC/AG'. At 37° C. in 1M Na+, the standard free energy of stack 'CT/GA' is −1.28 kcal/mol and the standard free energy of stack 'TC/AG' is −1.30 kcal/mol, so the standard free energy of 'CTC' pairing to 'GAG' is −2.58 kcal/mol.

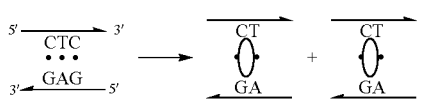

The $\Delta H°$ and $\Delta S°$ values of DNA-DNA stacks, based on published work by SantaLucia and Hicks are shown in Table 1. The standard enthalpy change and the standard entropy change of RNA-DNA stacks, based on published work by Sugimoto et al., are shown in Table 2. The standard enthalpy change and the standard entropy change of RNA-RNA stacks, based on published work by Turner et al., are shown in Table 3. The values of $\Delta H°$ for base stacks are accepted in the literature to be the same regardless of salinity. In contrast, the $\Delta S°$ of base stacks are adjusted by 0.368*ln([Na+]) cal/mol*K, regardless of nucleotide base identity, due to the electrostatic screening properties of cations. Additionally, divalent cations (such as $Mg^{2+}$) may also be used in the reaction solution; the effects of divalent cations on base pairing thermodynamics are described in the literature, such as by Owczarzy, Biochemistry, 2008. Finally, denaturants such as formamide may be used to facilitate hybridization reactions, particularly for in situ hybridization applications. It has been reported in literature that each percent (%) that water is replaced by formamide effectively increases the temperature by 0.6° C. for purposes of nucleic acid base pairing thermodynamics, see Blake and Delcourt, Nucleic Acids Research, 1996.

TABLE 1

Thermodynamic Parameters for DNA Watson-Crick Pairs in 1M NaCl.

| Propagation Sequence | $\Delta H°$ (kcal mol$^{-1}$) | $\Delta S°$ (e.u.) |
|---|---|---|
| AA/TT | −7.6 | −21.3 |
| AT/TA | −7.2 | −20.4 |
| TA/AT | −7.2 | −21.3 |
| CA/GT | −8.5 | −22.7 |
| GT/CA | −8.4 | −22.4 |
| CT/GA | −7.8 | −21.0 |
| GA/CT | −8.2 | −22.2 |
| CG/GC | −10.6 | −27.2 |
| GC/CG | −9.8 | −24.4 |
| GG/CC | −8.0 | −19.9 |
| Initiation | +0.2 | −5.7 |

TABLE 2

Thermodynamic Parameters for RNA-DNA Duplex Pairs in 1M NaCl.

| Sequence | $\Delta H°$/kcal mol$^{-1}$ | $\Delta S°$/kcal mol$^{-1}$ K$^{-1}$ |
|---|---|---|
| rAA dTT | −7.8 | −21.9 |
| rAC dTG | −5.9 | −12.3 |
| rAG dTC | −9.1 | −23.5 |
| rAU dTA | −8.3 | −23.9 |
| rCA dGT | −9.0 | −26.1 |
| rCC dGG | −9.3 | −23.2 |
| rCG dGC | −16.3 | −47.1 |
| rCU dGA | −7.0 | −19.7 |
| rGA dCT | −5.5 | −13.5 |
| rGC dCG | −8.0 | −17.1 |
| rGG dCC | −12.8 | −31.9 |
| rGU dCA | −7.8 | −21.6 |
| rUA dAT | −7.8 | −23.2 |
| rUC dAG | −8.6 | −22.9 |
| rUG dAC | −10.4 | −28.4 |
| rUU dAA | −11.5 | −36.4 |
| initiation | 1.9 | −3.9 |

TABLE 3

Thermodynamic Parameters for RNA-RNA Duplex Pairs in 1M NaCl.

| Sequence | $\Delta H°$/kcal mol$^{-1}$ | $\Delta S°$/cal mol$^{-1}$ K$^{-1}$ |
|---|---|---|
| AA/UU | −6.6 | −18.4 |
| AU/UA | −5.7 | −15.5 |
| AC/UG | −10.2 | −26.2 |
| AG/UC | −7.6 | −19.2 |
| UA/AU | −8.1 | −22.6 |
| UC/AG | −13.3 | −35.5 |
| UG/AC | −10.5 | −27.8 |
| CC/GG | −12.2 | −29.7 |
| CG/GC | −8.0 | −19.4 |
| GC/CG | −12.2 | −29.7 |
| Initiation | 0.0 | −10.8 |

In one instance, the reaction standard free energy ($\Delta G°_{rxn}$ from Expression 1 or 3) of hybridization for the various regions of the present probe system are calculated as described below.

$\Delta G°_{t-TC}$ (hybridization of target-toehold-region (region 6) to target-toehold-complementary regions (region 1)) is composed by summing the standard free energy of all toehold region nucleic acid stacks, the neighboring stack and an initiation energy penalty ($\Delta G°_{ini}$), due to the entropic loss of orienting two nucleic acid molecules for hybridization. The value of $\Delta G°_{ini}$ can be calculated from $\Delta H°_{ini}$ and $\Delta S°_{ini}$ via $\Delta G°=\Delta H°-\tau \Delta S°$

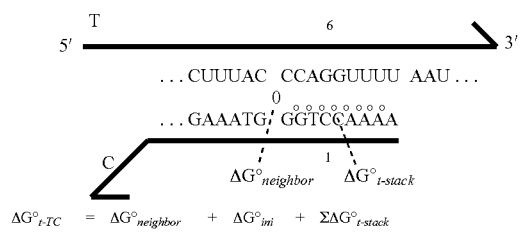

For DNA-DNA hybridization as provided in Table 1, $\Delta H°_{ini}$=0.2 kcal/mol and $\Delta S°_{ini}$=−5.7 cal/(mol·K). For RNA-DNA hybridization as provided in Table 2, $\Delta H°_{ini}$=1.9 kcal/mol and $\Delta S°_{ini}$=−3.9 cal/(mol·K). For RNA-RNA hybridization as provided in Table 3, $\Delta H°_{ini}$=0.0 kcal/mol and $\Delta S°_{ini}$=−10.8 cal/(mol·K).

In one instance, the probes described herein have a $\Delta G°_{t\text{-}TC}$ from about −2 kcal/mol to about −16 kcal/mol, from about −5 kcal/mol to about −13 kcal/mol, or from about −7 kcal/mol to about −10 kcal/mol at operation conditions.

$\Delta G°_{nh\text{-}PC}$ (hybridization of target-nonhomologous region 5 of protector P to target-nonhomologous-complementary region 3 of complement C) is composed by summing the standard free energy of all stacks in the non-homologous region, the neighboring stack on the homologous region, and the hybridization initiation energy $\Delta G°_{ini}$. Each stack standard free energy term and initiation standard free energy term is calculated based on the methods discussed above.

$\Delta G°_{v\text{-}TC}$ (hybridization of target-validation region 7 of target T to target-homologous-complementary region 2 of complement C) is equal to the sum of all nucleic acid stacks in the target-validation region. Each standard free energy term is calculated based on the methods discussed herein above. In this instance, the initiation energy $\Delta G°_{ini}$ is not applied in the calculation of this term.

$\Delta G°_{h\text{-}PC}$ (hybridization of target-homologous region 4 of protector P to target-homologous-complementary region 2 of complement C) is equal to the sum of all nucleic acid stacks in the target-homologous region. Each standard free energy term is calculated based on the methods discussed herein above. In this instance, the initiation energy $\Delta G°_{rxn}$ is not applied in the calculation of this term.

In one instance, the sum of the standard free energy of hybridization between the target-toehold-complementary region (region 1) and the target-toehold region (region 6) and between the target-homologous-complementary region (region 2) and the target-validation region (region 7) ($\Delta G°_{t\text{-}TC}+\Delta G°_{v\text{-}TC}$) is more negative than −7 kcal/mol, for example between about −7 kcal/mol and about −70 kcal/mol, between about −7 kcal/mol and about −50 kcal/mol, and between −7 kcal/mol and about −30 kcal/mol. In this instance or other instances, the sum of the standard free energy of hybridization between the target-nonhomologous-complementary region (region 3) and the target-nonhomologous region (region 5) and between the target-homologous region (region 4) and the target-homologous-complementary region (region 2) ($\Delta G°_{nh\text{-}PC}+\Delta G°_{h\text{-}PC}$) is more negative than −10 kcal/mol, for example between about −10 kcal/mol and about −70 kcal/mol, between about −10 kcal/mol and about −50 kcal/mol, and between −10 kcal/mol and about −30 kcal/mol.

In addition to enzyme-free nucleic acid detection systems, the probes of the present disclosure are useful in PCR application or other isothermal amplification systems as primer, for example, in hotspot multiplexing PCR reactions.

When applying the probes to PCR reactions, undesired amplification can be minimized after careful design and fine-tuning. Therefore, two or more primer systems for non-identical targets can be combined into one solution for hotspot multiplexing PCR. A schematic of hotspot multiplexing PCR is shown in FIG. 21. The sequences of targets in one multiplexing group can be highly similar due to the high specificity characteristic of the primer system. The design process for each primer system in the primer set is the same as that of the probes as described above. The specificity and sensitivity of each primer system could be adjusted according to experimental results. An example of primer systems for hotspot multiplexing PCR is shown in FIG. 22.

In one embodiment, the signal generation method for PCR or other isothermal amplification systems is using fluorophore-modified complement and quencher-modified protector. The protector would detach from the complement as the amplification proceeds, so the fluorescence signal is proportional to the copy number of amplified target. Different targets can be quantitated simultaneously by using spectral non-overlapping fluorophores. A similar signal generation method is using fluorophore-modified complement and quencher-modified protector as self-reporting primers as shown in FIG. 25. Another signal generation method that similar to traditional TaqMan probes is using fluorophore- and quencher-modified complement and non-modified protector as detection probes as shown in FIG. 26. In multiplexing setting, probes that bear different fluorophores can be used for different desired targets. Unlike traditional TaqMan probes that can be applied only when the desired targets are highly different, so that each TaqMan probe only specifically binds to one target and does not interfere with the reaction of other targets, the TaqMan-like probes presented in this disclosure may be uniquely advantageous in distinguishing similar targets.

Each probe system described herein may be comprised of DNA, RNA, or analogs thereof, and/or combinations thereof. In certain instances, a probe system comprises one or more non-natural nucleotides. The incorporation of non-natural nucleotides in the primers can further augment the performance of the probe systems, such as by providing improved per-base binding affinity and increased nuclease resistance.

The probe systems described herein may also be applied in the context of initiating enzymatic reactions; in such uses, the probe systems are referred to as primer systems, though the composition and method of action remains the same. Primer systems as described in this disclosure possess high specificity and capability for fine-tuning of performance, offering advantages to enzymatic assays of nucleic acids.

In certain instances, the primers described herein serve as starting points for polymerase extensions, including but not limited to polymerase chain reaction for replication of DNA templates, transcription for production of RNA from DNA templates, and reverse transcription for production of DNA from RNA templates, isothermal DNA and RNA amplification methods such as Nucleic Acid Sequence Based Amplification (NASBA), Loop mediated isothermal Amplification (LAMP), Helicase-Dependent Amplification (HDA), Recombinase Polymerase Amplification (RPA), isothermal Exponential Amplification Reaction (EXPAR), Nicking Enzyme Amplification Reaction (NEAR), Rolling Circle Amplification (RCA), and Transcription Mediated Amplification (TMA). The high specificity nature of the primers disclosed herein render them suitable for research and clinical applications in which only subsets of nucleic acids with particular sequences are to be extended and amplified.

A "target" for a probe system described herein can be any single-stranded nucleic acid, such as single-stranded DNA and single-stranded RNA, including double-stranded DNA and RNA rendered single-stranded through heat shock, asymmetric amplification, competitive binding, and other methods standard to the art. A "target" for a primer system can be any single-stranded (ss) or double-stranded (ds) nucleic acid, for example, DNA, RNA, or the DNA product of RNA subjected to reverse transcription. In some instances, a target may be a mixture (chimera) of DNA and RNA. In other instances, a target comprises artificial nucleic acid analogs, for example, peptide nucleic acids (Nielsen et al. Science 254(5037): 1497-500 (1991)) or locked nucleic acids (Alexei et al. Tetrahedron 54(14): 3607-30 (1998)). In some instances, a target may be naturally occurring (e.g., genomic DNA) or it may be synthetic (e.g., from a genomic library). As used herein, a "naturally occurring" nucleic acid sequence is a sequence that is present in nucleic acid molecules of organisms or viruses that exist in nature in the absence of human intervention. In some instances, a target is genomic DNA, messenger RNA, ribosomal RNA, micro-RNA, pre-micro-RNA, pro-micro-RNA, long non-coding RNA, small RNA, epigenetically modified DNA, epigenetically modified RNA, viral DNA, viral RNA or piwi-RNA. In certain instances, a target nucleic acid is a nucleic acid that naturally occurs in an organism or virus. In some instances, a target nucleic is the nucleic acid of a pathogenic organism or virus. In certain instances the presence or absence of a target nucleic acid in a subject is indicative that the subject has a disease or disorder or is predisposed to acquire a disease or disorder. In certain instances the presence or absence of a target nucleic acid in a subject is indicative that the subject will respond well or poorly to a treatment, such as a drug, to treat a disease or disorder. In certain instances the presence or absence of a target nucleic acid in a subject is indicative that the subject who has been treated previously for cancer and is in remission may be at risk of cancer recurrence.

The terms "polynucleotide," "nucleic acid," "oligonucleotide," and "nucleic acid molecule" are used interchangeably. They refer to a polymeric form of nucleotides of any length, either deoxyribonucleotides or ribonucleotides, or analogs thereof. Polynucleotides may have any three-dimensional structure, and may perform any function. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. A polynucleotide may be further modified, such as by conjugation with a labeling component. The term "recombinant" polynucleotide means a polynucleotide of genomic, cDNA, semi-synthetic, or synthetic origin which either does not occur in nature or is linked to another polynucleotide in a non-natural arrangement. The term "isolated nucleic acid" refers to a polynucleotide of natural or synthetic origin or some combination thereof, which (1) is not associated with the cell in which the "isolated nucleic acid" is found in nature, and/or (2) is operably linked to a polynucleotide to which it is not linked in nature.

A nucleic acid may also encompass single- and double-stranded DNA and RNA, as well as any and all forms of alternative nucleic acid containing modified bases, sugars, and backbones. The term "nucleic acid" thus will be understood to include, but not be limited to, single- or double-stranded DNA or RNA (and forms thereof that can be partially single-stranded or partially double-stranded), cDNA, aptamers, peptide nucleic acids ("PNA"), 2'-5' DNA (a synthetic material with a shortened backbone that has a base-spacing that matches the A conformation of DNA; 2'-5' DNA will not normally hybridize with DNA in the B form, but it will hybridize readily with RNA), and locked nucleic acids ("LNA"). Nucleic acid analogues include known analogues of natural nucleotides that have similar or improved binding, hybridization of base-pairing properties. "Analogous" forms of purines and pyrimidines are well known in the art, and include, but are not limited to aziridinylcytosine, 4-acetylcytosine, 5-fluorouracil, 5-bromouracil, 5-carboxymethylaminomethyl-2-thiouracil, 5-carboxymethylaminomethyluracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N.sup.6-methyl adenine, 7-methylguanine, 5-methylaminomethyluracil, 5-methoxyaminomethyl-2-thiouracil, beta-D-mannosylqueosine, 5-methoxyuracil, 2-methylthio-N6-isopentenyladenine, uracil-5-oxyacetic acid methylester, pseudouracil, queosine, 2-thiocytosine, 5-methyl-2-thiouracil, 2-thiouracil, 4-thiouracil, 5-methyluracil, uracil-5-oxyacetic acid, and 2,6-diaminopurine. DNA backbone analogues provided herein include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs), methylphosphonate linkages or alternating methylphosphonate and phosphodiester linkages (Strauss-Soukup, 1997, Biochemistry 36:8692-8698), and benzylphosphonate linkages, as discussed in U.S. Pat. No. 6,664,057; see also OLIGO-NUCLEOTIDES AND ANALOGUES, A PRACTICAL APPROACH, edited by F. Eckstein, IRL Press at Oxford University Press (1991); Antisense Strategies, Annals of the New York Academy of Sciences, Volume 600, Eds. Baserga and Denhardt (NYAS 1992); Milligan, 1993, J. Med. Chem. 36: 1923-1937; Antisense Research and Applications (1993, CRC Press). The nucleic acids herein can be extracted from cells or synthetically prepared according to any means known to those skilled in the art; for example, the nucleic acids can be chemically synthesized or transcribed or reverse transcribed from cDNA or mRNA, among other sources.

A target nucleic acid utilized herein can be any nucleic acid, for example, human nucleic acids, bacterial nucleic acids, or viral nucleic acids. A target nucleic acid sample or sample comprising a target nucleic acid can be, for example, a nucleic acid sample from one or more biological samples including, but not limited to whole blood, nucleic acids extracted from whole blood, plasma, nucleic acids extracted from plasma, sputum, stool, urine, cheek or nasal swab. cells, tissues, or bodily fluids. Target biological samples can be derived from any source including, but not limited to, eukaryotes, plants, animals, vertebrates, fish, mammals, humans, non-humans, bacteria, microbes, viruses, biological sources, serum, plasma, blood, urine, semen, lymphatic fluid, cerebrospinal fluid, amniotic fluid, biopsies, needle aspiration biopsies, cancers, tumors, tissues, cells, cell lysates, crude cell lysates, tissue lysates, tissue culture cells, buccal swabs, mouthwashes, stool, mummified tissue, forensic sources, autopsies, archeological sources, infections, nosocomial infections, production sources, drug preparations, biological molecule productions, protein preparations, lipid preparations, carbohydrate preparations, inanimate objects, air, soil, sap, metal, fossils, excavated materials, and/or other terrestrial or extra-terrestrial materials and sources. The sample may also contain mixtures of material from one source or different sources. For example, nucleic acids of an infecting bacterium or virus can be amplified along with human nucleic acids when nucleic acids from such infected cells or tissues are amplified using the disclosed methods. Types of useful target samples include eukaryotic samples, plant samples, animal samples, vertebrate samples, fish samples, mammalian samples, human samples, non-human samples, bacterial samples, microbial samples, viral samples, biological samples, serum samples, plasma samples, blood samples, urine samples, semen samples, lymphatic fluid samples, cerebrospinal fluid samples, amniotic fluid samples, biopsy samples, needle aspiration biopsy samples, cancer samples, tumor samples, tissue samples, cell samples, cell lysate samples, crude cell lysate samples, tissue lysate samples, tissue culture cell samples, buccal swab samples, mouthwash samples, stool samples, mummified tissue samples, autopsy samples, archeological samples, infection samples, nosocomial infection samples, production samples, drug preparation samples, biological molecule production samples, protein preparation samples, lipid preparation samples, carbohydrate preparation samples, inanimate object samples, air samples, soil samples, sap samples, metal samples, fossil samples, excavated material samples, and/or other terrestrial or extra-terrestrial samples. In some instances, a target nucleic acids utilized herein comprise repetitive sequence, secondary structure, and/or a high G/C content.

In certain instances, a target nucleic acid molecule of interest is about 19 to about 1,000,000 nucleotides (nt) in length. In some instances, the target is about 19 to about 100, about 100 to about 1000, about 1000 to about 10,000, about 10,000 to about 100,000, or about 100,000 to about 1,000,000 nucleotides in length. In some instances, the target is about 20, about 100, about 200, about 300, about 400, about 500, about 600, about 700, about 800, about 900, about 1,000, about 2,000, about 3,000, about 4,000, about 5,000, about 6,000, about 7,000, about 8,000, about 9000, about 10,000, about 20,000, about 30,000, about 40,000, about 50,000, about 60,000, about 70,000, about 80,000, about 90,000, about 100,000, about 200,000, about 300,000, about 400,000, about 500,000, about 600,000, about 700,000, about 800,000, about 900,000, or about 1,000,000 nucleotides in length. It is to be understood that the target nucleic acid may be provided in the context of a longer nucleic acid (e.g., such as a coding sequence or gene within a chromosome or a chromosome fragment).

In certain instances, a target of interest is linear, while in other instances, a target is circular (e.g., plasmid DNA, mitochondrial DNA, or plastid DNA).

In some instances, provided herein are primer-target systems. A primer-target system comprises one or more nucleic acid targets, a polymerase, and one or more primers (e.g., primer duplex). The term "primer" encompasses any one of the primers or primer systems described herein. In certain instances, the primer-target systems described herein comprise a plurality of different primers. In some instances, a primer-target system can comprise at least two primers, which can be used to identify and, for example amplify, a target nucleic acid molecule. A target nucleic acid molecule may be present amongst a plurality of non-target nucleic acid molecules, for example, as a single copy or in low copy number. Any one of the primer-target systems described herein may comprises conditions similar to those used in nucleic acid amplification or sequencing reactions (e.g., similar reagents, reaction temperature, etc.).

Provided herein are kits comprising (1) at least one complement strand having a target-homologous-complementary region (region 2), a target-nonhomologous-complementary region (region 3), and a target-toehold-complementary region (region 1), and (2) at least one protector strand having a target-homologous region (region 4) and a target-nonhomologous region (region 5). Provided herein are kits comprising at least one primer duplex comprising (1) at least one complement strand having a target-homologous-complementary region, a target-nonhomologous-complementary region, and a target-toehold-complementary region, and (2) at least one protector strand having a target-homologous region and a target-nonhomologous region.

Any one of the kits described herein may further comprise a polymerase, including reverse transcriptase. Any one of the kits provided herein may further comprise one or more agent selected from buffer (e.g., KC1, MgCl2, Tris-HCl), dNTPs (e.g., dATP, dCTP, dGTP, dTTP), and water. Any one of the kits provided herein may comprise protector strand is molar excess of the primer. Any one of the kits provided herein may further comprise instructions or directions for obtaining instructions (e.g., from a website) for using the components of the kits. Any one of the kits provided herein may further comprise at least one reaction tube, well, chamber, or the like.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

The use of the word "a" or "an" when used in conjunction with the term "comprising" in the claims and/or the specification may mean "one," but it is also consistent with the meaning of "one or more," "at least one," and "one or more than one." As used herein "another" may mean at least a second or more.

It is contemplated that any instance discussed in this specification can be implemented with respect to any method or composition of the invention, and vice versa. Furthermore, compositions of the invention can be used to achieve the methods of the invention.

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

To facilitate a better understanding of the present invention, the following examples of specific instances are given. In no way should the following examples be read to limit or define the entire scope of the invention.

EXAMPLES

Twelve examples of DNA probe systems to an RNA target are shown in FIGS. 9-20.

The following examples demonstrate the design principles, illustrate the mathematics of reaction standard free energy)($\Delta G°$) calculations for the different regions, and exemplify typical probe systems generated in the method described in the present disclosure. These representative examples cover a range of different biological target sequences, are computed for a number of different operation temperatures and salinities. Example 11 furthermore shows the design of a probe intended to operate in a concentration of the denaturant formamide. Also given are the stoichiometric ratios $[P]_0/[C]_0$ needed to satisfy the standard free energy value of Expression 1 being equal to the standard free energy value of Expression 2.

the value provided by the $\Delta G°_{rxn}$ according to Expression 1 to have value identical to that provided by Expression 2 is also provided in Table 4. Finally, the X value provides for the variation in Expression 2 to obtain a value equal to Expression 1 given the corresponding stoichiometric ratios and was 0.00, 1.42, and −1.27 kcal/mol, respectively.

Example 2

Example 2 provides a probe directed to the target nucleic acid BRAF 71-90 as shown in FIG. 10. The following $\Delta G°$ values for hybridization of the probe to the target at 37° C., 1M Na$^+$ are provided in Table 4: (1) hybridization of target homologous complementary region 2 of complement strand C to target homologous region 4 of protector strand P ($\Delta G°_{h\text{-}PC}$); (2) hybridization of target-nonhomologous-complementary region 3 of complement strand C to target-nonhomologous region 5 of protect strand P ($\Delta G°_{nh\text{-}PC}$); (3) hybridization of target-homologous complementary region 2 of complement strand C to target-validation region 7 of target T ($\Delta G°_{v\text{-}TC}$); (4) hybridization of target-toehold-complementary region 1 of complement strand C to target-toehold region 6 of target T ($\Delta G°_{t\text{-}TC}$); and (5) $\Delta G°_{rxn}$ which is $\Delta G°_{t\text{-}TC} - \Delta G°_{nh\text{-}PC} + (\Delta G°_{v\text{-}TC} - \Delta G°_{h\text{-}PC})$ (Expression 1). In addition, the stoichiometric ratio ($[P]_0/[C]_0$) that allows the value provided by the $\Delta G°_{rxn}$ according to Expression 1 to have value identical to that provided by Expression 2 is also provided in Table 4.

TABLE 4

Standard free energy and stoichiometric data for the probes of Examples 1-12.

| Ex. | $\Delta G°_{h\text{-}PC}$ (kcal/mol) | $\Delta G°_{nh\text{-}PC}$ (kcal/mol) | $\Delta G°_{v\text{-}TC}$ (kcal/mol) | $\Delta G°_{t\text{-}TC}$ (kcal/mol) | $\Delta G°_{rxn}$ (kcal/mol) | $\frac{([P]_0 - [C]_0)}{[C]_0}$ | $\frac{[P]_0}{[C]_0}$ |
|---|---|---|---|---|---|---|---|
| 1 | −24.16 | −11.68 | −27.60 | −8.09 | 0.15 | 0.78 | 1.78 |
|   |        |        |        |       |      | 7.8  | 8.8  |
|   |        |        |        |       |      | 0.1  | 1.10 |
| 2 | −28.45 | −10.02 | −32.83 | −6.26 | −0.61 | 2.69 | 3.69 |
| 3 | −31.15 | −7.71  | −26.44 | −8.61 | −1.54 | 12.14 | 13.14 |
| 4 | −17.06 | −9.59  | −16.75 | −10.36 | −0.46 | 2.11 | 3.11 |
| 5 | −11.68 | −9.20  | −13.42 | −8.94 | −1.49 | 11.2 | 12.2 |
| 6 | −25.43 | −5.25  | −21.76 | −9.12 | −0.22 | 1.43 | 2.43 |
| 7 | −12.95 | −14.35 | −15.94 | −10.33 | 1.03 | 0.19 | 1.19 |
| 8 | −31.64 | −11.59 | −34.77 | −8.73 | −0.27 | 1.55 | 2.55 |
| 9 | −22.50 | −14.81 | −28.20 | −9.48 | −0.37 | 1.82 | 2.82 |
| 10 | −19.12 | −9.45 | −19.84 | −9.39 | −0.66 | 3.00 | 4.00 |
| 11 | −20.56 | −11.09 | −22.58 | −8.75 | 0.32 | 0.58 | 1.58 |
| 12 | −7.45 | −4.43 | −7.54 | −7.50 | −3.07 | 100.0 | 101.0 |

Example 1

Example 1 provides a probe directed to the target nucleic acid BRAF 11-30 as shown in FIG. 9. The following $\Delta G°$ values for hybridization of the probe to the target at 37° C., 1M Na$^+$ are provided in Table 4: (1) hybridization of target homologous complementary region 2 of complement strand C to target homologous region 4 of protector strand P ($\Delta G°_{h\text{-}PC}$); (2) hybridization of target-nonhomologous-complementary region 3 of complement strand C to target-nonhomologous region 5 of protect strand P ($\Delta G°_{nh\text{-}PC}$); (3) hybridization of target-homologous complementary region 2 of complement strand C to target-validation region 7 of target T ($\Delta G°_{v\text{-}TC}$); (4) hybridization of target-toehold-complementary region 1 of complement strand C to target-toehold region 6 of target T ($\Delta G°_{t\text{-}TC}$); and (5) $\Delta G°_{rxn}$ which is $\Delta G°_{t\text{-}TC} - \Delta G°_{nh\text{-}PC} + (\Delta G°_{v\text{-}TC} - \Delta G°_{h\text{-}PC})$ (Expression 1). In addition, the stoichiometric ratio ($[P]_0/[C]_0$) that allows Example 3

Example 3 provides a probe directed to the target nucleic acid BRAF 131-160 as shown in FIG. 11. The following $\Delta G°$ values for hybridization of the probe to the target at 37° C., 1M Na$^+$ are provided in Table 4: (1) hybridization of target homologous complementary region 2 of complement strand C to target homologous region 4 of protector strand P ($\Delta G°_{h\text{-}PC}$); (2) hybridization of target-nonhomologous-complementary region 3 of complement strand C to target-nonhomologous region 5 of protect strand P ($\Delta G°_{nh\text{-}PC}$); (3) hybridization of target-homologous complementary region 2 of complement strand C to target-validation region 7 of target T ($\Delta G°_{v\text{-}TC}$); (4) hybridization of target-toehold-complementary region 1 of complement strand C to target-toehold region 6 of target T ($\Delta G°_{t\text{-}TC}$); and (5) $\Delta G°_{rxn}$ which is $\Delta G°_{t\text{-}TC} - \Delta G°_{nh\text{-}PC} + (\Delta G°_{v\text{-}TC} - \Delta G°_{h\text{-}PC})$ (Expression 1). In addition, the stoichiometric ratio ($[P]_0/[C]_0$) that allows the value provided by the $\Delta G°_{rxn}$ according to Expression 1 to have value identical to that provided by Expression 2 is also provided in Table 4.

Example 4

Example 4 provides a probe directed to the target nucleic acid BRAF 191-220 as shown in FIG. 12. The following $\Delta G°$ values for hybridization of the probe to the target at 52° C., 1M Na$^+$ are provided in Table 4: (1) hybridization of target homologous complementary region 2 of complement strand C to target homologous region 4 of protector strand P ($\Delta G°_{h-PC}$); (2) hybridization of target-nonhomologous-complementary region 3 of complement strand C to target-nonhomologous region 5 of protect strand P ($\Delta G°_{nh-PC}$); (3) hybridization of target-homologous complementary region 2 of complement strand C to target-validation region 7 of target T ($\Delta G°_{v-TC}$); (4) hybridization of target-toehold-complementary region 1 of complement strand C to target-toehold region 6 of target T ($\Delta G°_{t-TC}$); and (5) $\Delta G°_{rxn}$ which is $\Delta G°_{t-TC} - \Delta G°_{nh-PC} + (\Delta G°_{v-TC} - \Delta G°_{h-PC})$ (Expression 1). In addition, the stoichiometric ratio ($[P]_0/[C]_0$) that allows the value provided by the $\Delta G°_{rxn}$ according to Expression 1 to have value identical to that provided by Expression 2 is also provided in Table 4.

Example 5

Example 5 provides a probe directed to the target nucleic acid BRAF 251-280 as shown in FIG. 13. The following $\Delta G°$ values for hybridization of the probe to the target at 65° C., 1M Na$^+$ are provided in Table 4: (1) hybridization of target homologous complementary region 2 of complement strand C to target homologous region 4 of protector strand P ($\Delta G°_{h-PC}$); (2) hybridization of target-nonhomologous-complementary region 3 of complement strand C to target-nonhomologous region 5 of protect strand P ($\Delta G°_{nh-PC}$); (3) hybridization of target-homologous complementary region 2 of complement strand C to target-validation region 7 of target T ($\Delta G°_{v-TC}$); (4) hybridization of target-toehold-complementary region 1 of complement strand C to target-toehold region 6 of target T ($\Delta G°_{t-TC}$); and (5) $\Delta G°_{rxn}$ which is $\Delta G°_{t-TC} - \Delta G°_{nh-PC} + (\Delta G°_{v-TC} - \Delta G°_{h-PC})$ (Expression 1). In addition, the stoichiometric ratio ($[P]_0/[C]_0$) that allows the value provided by the $\Delta G°_{rxn}$ according to Expression 1 to have value identical to that provided by Expression 2 is also provided in Table 4.

Example 6

Example 6 provides a probe directed to the target nucleic acid BRAF 311-350 as shown in FIG. 14. The following $\Delta G°$ values for hybridization of the probe to the target at 52° C., 1M Na$^+$ are provided in Table 4: (1) hybridization of target homologous complementary region 2 of complement strand C to target homologous region 4 of protector strand P ($\Delta G°_{h-PC}$); (2) hybridization of target-nonhomologous-complementary region 3 of complement strand C to target-nonhomologous region 5 of protect strand P ($\Delta G°_{nh-PC}$); (3) hybridization of target-homologous complementary region 2 of complement strand C to target-validation region 7 of target T ($\Delta G°_{v-TC}$); (4) hybridization of target-toehold-complementary region 1 of complement strand C to target-toehold region 6 of target T ($\Delta G°_{t-TC}$); and (5) $\Delta G°_{rxn}$ which is $\Delta G°_{t-TC} - \Delta G°_{nh-PC} + (\Delta G°_{v-TC} \Delta G°_{h-PC})$ (Expression 1). In addition, the stoichiometric ratio ($[P]_0/[C]_0$) that allows the value provided by the $\Delta G°_{rxn}$ according to Expression 1 to have value identical to that provided by Expression 2 is also provided in Table 4.

Example 7

Example 7 provides a probe directed to the target nucleic acid BRAF 431-460 as shown in FIG. 15. The following $\Delta G°$ values for hybridization of the probe to the target at 65° C., 1M Na$^+$ are provided in Table 4: (1) hybridization of target homologous complementary region 2 of complement strand C to target homologous region 4 of protector strand P ($\Delta G°_{h-PC}$); (2) hybridization of target-nonhomologous-complementary region 3 of complement strand C to target-nonhomologous region 5 of protect strand P ($\Delta G°_{nh-PC}$); (3) hybridization of target-homologous complementary region 2 of complement strand C to target-validation region 7 of target T ($\Delta G°_{v-TC}$); (4) hybridization of target-toehold-complementary region 1 of complement strand C to target-toehold region 6 of target T ($\Delta G°_{t-TC}$); and (5) $\Delta G°_{rxn}$ which is $\Delta G°_{t-TC} - \Delta G°_{nh-PC} + (\Delta G°_{v-TC} - \Delta G°_{h-PC})$ (Expression 1). In addition, the stoichiometric ratio ($[P]_0/[C]_0$) that allows the value provided by the $\Delta G°_{rxn}$ according to Expression 1 to have value identical to that provided by Expression 2 is also provided in Table 4.

Example 8

Example 8 provides a probe directed to the target nucleic acid BRAF 491-520 as shown in FIG. 16. The following $\Delta G°$ values for hybridization of the probe to the target at 37° C., 1M Na$^+$ are provided in Table 4: (1) hybridization of target homologous complementary region 2 of complement strand C to target homologous region 4 of protector strand P ($\Delta G°_{v-TC}$); (2) hybridization of target-nonhomologous-complementary region 3 of complement strand C to target-nonhomologous region 5 of protect strand P ($\Delta G°_{nh-PC}$); (3) hybridization of target-homologous complementary region 2 of complement strand C to target-validation region 7 of target T ($\Delta G°_{v-TC}$); (4) hybridization of target-toehold-complementary region 1 of complement strand C to target-toehold region 6 of target T ($\Delta G°_{t-TC}$); and (5) $\Delta G°_{rxn}$ which is $\Delta G°_{t-TC} - \Delta G°_{nh-PC} + (\Delta G°_{v-TC} - \Delta G°_{h-PC})$ (Expression 1). In addition, the stoichiometric ratio ($[P]_0/[C]_0$) that allows the value provided by the $\Delta G°_{rxn}$ according to Expression 1 to have value identical to that provided by Expression 2 is also provided in Table 4.

Example 9

Example 9 provides a probe directed to the target nucleic acid BRAF 551-580 as shown in FIG. 17. The following $\Delta G°$ values for hybridization of the probe to the target at 37° C., 1M Na$^+$ are provided in Table 4: (1) hybridization of target homologous complementary region 2 of complement strand C to target homologous region 4 of protector strand P ($\Delta G°_{h-PC}$); (2) hybridization of target-nonhomologous-complementary region 3 of complement strand C to target-nonhomologous region 5 of protect strand P ($\Delta G°_{nh-PC}$); (3) hybridization of target-homologous complementary region 2 of complement strand C to target-validation region 7 of target T ($\Delta G°_{v-TC}$); (4) hybridization of target-toehold-complementary region 1 of complement strand C to target-toehold region 6 of target T ($\Delta G°_{t-TC}$); and (5) $\Delta G°_{rxn}$ which is $\Delta G°_{t-TC} - \Delta G°_{nh-PC} + (\Delta G°_{v-TC} \Delta G°_{h-PC})$ (Expression 1). In addition, the stoichiometric ratio ($[P]_0/[C]_0$) that allows the value provided by the $\Delta G°_{rxn}$ according to Expression 1 to have value identical to that provided by Expression 2 is also provided in Table 4.

Example 10

Example 10 provides a probe directed to the target nucleic acid BRAF 611-630 as shown in FIG. 18. The following $\Delta G°$ values for hybridization of the probe to the target at 25° C., 1M Na$^+$ are provided in Table 4: (1) hybridization of target homologous complementary region 2 of complement strand C to target homologous region 4 of protector strand P ($\Delta G°_{h-PC}$); (2) hybridization of target-nonhomologous-complementary region 3 of complement strand C to target-nonhomologous region 5 of protect strand P ($\Delta G°_{nh-PC}$); (3) hybridization of target-homologous complementary region 2 of complement strand C to target-validation region 7 of target T ($\Delta G°_{v-TC}$); (4) hybridization of target-toehold-complementary region 1 of complement strand C to target-toehold region 6 of target T ($\Delta G°_{t-TC}$); and (5) $\Delta G°_{rxn}$ which is $\Delta G°_{t-TC} - \Delta G°_{nh-PC} + (\Delta G°_{v-TC} \Delta G°_{h-PC})$ (Expression 1). In addition, the stoichiometric ratio ($[P]_0/[C]_0$) that allows the value provided by the $\Delta G°_{rxn}$ according to Expression 1 to have value identical to that provided by Expression 2 is also provided in Table 4.

Example 11

Example 11 provides a probe directed to the target nucleic acid BRAF 670-700 as shown in FIG. 19. The following $\Delta G°$ values for hybridization of the probe to the target at 25° C., 1M Na$^+$ in 30% formamide are provided in Table 4: (1) hybridization of target homologous complementary region 2 of complement strand C to target homologous region 4 of protector strand P ($\Delta G°_{h-PC}$); (2) hybridization of target-nonhomologous-complementary region 3 of complement strand C to target-nonhomologous region 5 of protect strand P ($\Delta G°_{nh-PC}$); (3) hybridization of target-homologous complementary region 2 of complement strand C to target-validation region 7 of target T ($\Delta G°_{v-TC}$); (4) hybridization of target-toehold-complementary region 1 of complement strand C to target-toehold region 6 of target T ($\Delta G°_{t-TC}$); and (5) $\Delta G°_{rxn}$ which is $\Delta G°_{t-TC} - \Delta G°_{nh-PC} (\Delta G°_{v-TC} - \Delta G°_{h-PC})$ (Expression 1). In addition, the stoichiometric ratio ($[P]_0/[C]_0$) that allows the value provided by the $\Delta G°_{rxn}$ according to Expression 1 to have value identical to that provided by Expression 2 is also provided in Table 4.

Example 12

Example 12 provides a probe directed to a DNA target nucleic acid as shown in FIG. 20. The following $\Delta G°$ values for hybridization of the probe to the target at 62° C., 3 mM Mg$^{2+}$ are provided in Table 4: (1) hybridization of target homologous complementary region 2 of complement strand C to target homologous region 4 of protector strand P ($\Delta G°_{h-PC}$); (2) hybridization of target-nonhomologous-complementary region 3 of complement strand C to target-nonhomologous region 5 of protect strand P ($\Delta G°_{nh-PC}$); (3) hybridization of target-homologous complementary region 2 of complement strand C to target-validation region 7 of target T ($\Delta G°_{v-TC}$); (4) hybridization of target-toehold-complementary region 1 of complement strand C to target-toehold region 6 of target T ($\Delta G°_{t-TC}$); and (5) $\Delta G°_{rxn}$ which is $\Delta G°_{t-TC} - \Delta G°_{nh-PC} + (\Delta G°_{v-TC} - \Delta G°_{h-PC})$ (Expression 1). In addition, the stoichiometric ratio ($[P]_0/[C]_0$) that allows the value provided by the $\Delta G°_{rxn}$ according to Expression 1 to have value identical to that provided by Expression 2 is also provided in Table 4.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements as well as experimental error in literature-reported values.

Therefore, the present invention is well adapted to attain the ends and advantages mentioned as well as those that are inherent therein. While numerous changes may be made by those skilled in the art, such changes are encompassed within the spirit of this invention as illustrated, in part, by the appended claims.

What is claimed is:

1. A composition comprising:
a first nucleic acid strand comprising a first region, a second region, and a third region; and a second nucleic acid strand comprising a fourth region and a fifth region;
wherein the first region is capable of hybridizing to a sixth region of a target nucleic acid, the second region is capable of hybridizing, independently, to each of the fourth region of the second nucleic acid strand and to a seventh region of the target nucleic acid, and the third region is capable of hybridizing to the fifth region of the second nucleic acid strand;
wherein the third region comprises at least seven nucleotides, wherein the third region is not capable of hybridizing to the seventh region of the target nucleic acid or a region of the target nucleic acid that is adjacent to the seventh region;
wherein the first nucleic acid strand is present at a first concentration and the second nucleic acid strand is present at a second concentration, wherein the second concentration is greater than the first concentration;
wherein each of the first nucleic acid strand and the second nucleic acid strand comprise a specific nucleic acid sequence such that hybridization of the first nucleic acid strand to the second nucleic acid strand and hybridization of the first nucleic acid strand to the target nucleic acid, when the hybridization of the first nucleic acid strand to the second nucleic acid strand and the hybridization of the first nucleic acid strand to the target nucleic acid are performed in a single reaction mixture comprising the first nucleic acid strand, the second nucleic acid strand, and the target nucleic acid, has a reaction standard free energy as determined by Expression 1 [$\Delta G°_{t\text{-}TC}-\Delta G°_{nh\text{-}PC}+(\Delta G°_{v\text{-}TC}-\Delta G°_{h\text{-}PC})$] and the difference between the reaction standard free energy determined by Expression 1 and a reaction free energy as determined by Expression 2 [$-R\tau \ln(([P]_0 - [C]_0)/[C]_0)$] is within 5 kcal/mol,
wherein the reaction free energy as determined by Expression 2 is an estimated reaction standard free energy of a hybridization reaction of a probe system comprising the first nucleic acid strand and the second nucleic acid strand with the target nucleic acid, the $[P]_0$ term of Expression 2 equals the second concentration, the $[C]_0$ term of Expression 2 equals the first concentration, the R term of Expression 2 equals the universal gas constant 8.314 J/mol·K, and the $\tau$ term of Expression 2 equals the temperature of the single reaction mixture in Kelvin; and
wherein the $\Delta G°_{t\text{-}TC}$ term of Expression 1 represents the standard free energy of hybridization between the sixth region and the first region, wherein the $\Delta G°_{nh\text{-}PC}$ term of Expression 1 represents the standard free energy of hybridization between the fifth region and the third region, wherein the $\Delta G°_{v\text{-}TC}$ term of Expression 1 represents the standard free energy of hybridization between the seventh region and the second region, and wherein the $\Delta G°_{h\text{-}PC}$ term of Expression 1 represents the standard free energy of hybridization between the fourth region and the second region, and
wherein the values for $\Delta G°_{t\text{-}TC}$ and $\Delta G°_{nh\text{-}PC}$ differ by more than 10%.

2. The composition of claim 1 further comprising a label conjugated to the first nucleic acid strand and wherein the label is selected from the group consisting of organic fluorophores, haptens, nanoparticles, and radioisotopes.

3. The composition of claim 2 further comprising a label conjugated to the second nucleic acid strand and wherein the label is selected from the group consisting of organic fluorophores, haptens, nanoparticles, and radioisotopes such that Expression 3 [$\Delta G°_{t\text{-}TC}-\Delta G°_{nh\text{-}PC}+(\Delta G°_{v\text{-}TC}-\Delta G°_{h\text{-}PC}+\Delta G°_{label}$] is used to substitute Expression 1 for determining the reaction standard free energy of the hybridization of the first nucleic acid strand to the second nucleic acid strand and the hybridization of the first nucleic acid strand to the target nucleic acid, wherein $\Delta G°_{label}$ term of Expression 3 equals a standard free energy of the label conjugated to the first nucleic acid strand minus a standard free energy of an interaction between the label conjugated to the first nucleic acid strand and the label conjugated to the second nucleic acid strand.

4. The composition of claim 1 wherein the value of $\Delta G°_{t\text{-}TC}-\Delta G°_{nh\text{-}Pc}$ is not between −1 kcal/mol and +1 kcal/mol.

5. The composition of claim 1 wherein $\Delta G°_{t\text{-}TC}$ is about −2 kcal/mol to about −16 kcal/mol.

6. The composition of claim 1 wherein the first nucleic acid strand and the second nucleic acid strand form a partially double-stranded nucleic acid probe or primer.

7. A composition comprising:
a first nucleic acid strand comprising a first region, a second region, and a third region, and a second nucleic acid strand comprising a fourth region and a fifth region, wherein said first region possesses a nucleotide sequence that is complementary to a nucleotide sequence of a sixth region of a target nucleic acid molecule, wherein the second region possesses a nucleotide sequence that is complementary to a nucleotide sequence of a seventh region of the target nucleic acid molecule, wherein the third region comprises at least seven nucleotides, wherein the third region is not capable of hybridizing to the seventh region of the target nucleic acid or to a region of the target nucleic acid that is adjacent to the seventh region;

wherein the fourth region possesses a nucleotide sequence that is complementary to the nucleotide sequence of the second region, and wherein the fifth region possesses a nucleotide sequence that is complementary to the nucleotide sequence of the third region;

wherein each of the first nucleic acid strand and the second nucleic acid strand comprise a specific nucleic acid sequence such that hybridization of the first nucleic acid strand to the second nucleic acid strand and hybridization of the first nucleic acid strand to the target nucleic acid molecule, when the hybridization of the first nucleic acid strand to the second nucleic acid strand and the hybridization of the first nucleic acid strand to the target nucleic acid molecule are performed in a single reaction mixture comprising the first nucleic acid strand, the second nucleic acid strand, and the target nucleic acid molecule, has a reaction standard free energy from about −4 kcal/mol to about +4 kcal/mol, wherein the reaction standard free energy is determined by Expression 1 [$\Delta G°_{t-TC} - \Delta G°_{nh-PC} + (\Delta G°_{v-TC} - \Delta G°_{h-PC})$], wherein the $\Delta G°_{t-TC}$ term of Expression 1 represents the standard free energy of hybridization between the first region and the sixth region, wherein the $\Delta G°_{nh-PC}$ term of Expression 1 represents the free energy of hybridization between the third region and the fifth region, wherein the $\Delta G°_{v-TC}$ term of Expression 1 represents the standard free energy of hybridization between the seventh region and the second region, and wherein the $\Delta G°_{h-PC}$ term of Expression 1 represents the standard free energy of hybridization between the fourth region and the second region, and wherein the values for $\Delta G°_{t-Tc}$ and $\Delta G20_{nh-Pc}$ differ by more than 10%.

8. The composition of claim 7 comprising a first concentration of the first nucleic acid strand and a second concentration of the second nucleic acid strand, wherein the difference between the reaction standard free energy of the hybridization of the first nucleic acid strand to the second nucleic acid strand and the hybridization of the first nucleic acid strand to the target nucleic acid molecule as determined by Expression 1 and a reaction free energy as determined by Expression 2 [$-R\tau \ln(([P]_0-[C]_0/[C]_0))$] is within 3 kcal/mol, wherein the reaction free energy as determined by Expression 2 is an estimated reaction standard free energy of a hybridization reaction of a probe system comprising the first nucleic acid strand and the second nucleic acid strand with the target nucleic acid molecule, the $[P]_0$ term of Expression 2 equals the second concentration, the $[C]_0$ term of Expression 2 equals the first concentration, the R term of Expression 2 equals the universal gas constant 8.314 J/mol·K, and the $\tau$ term of Expression 2 equals the temperature of the single reaction mixture in Kelvin.

9. The composition of claim 7 wherein $\Delta G°_{t-TC}$ is about −5 kcal/mol to about −15 kcal/mol.

10. The composition of claim 7 wherein the first nucleic acid strand and the second nucleic acid strand form a partially double-stranded nucleic acid molecule, and wherein the first region possesses no secondary structure.

11. The composition of claim 7 wherein the sum of the standard free energy of the hybridization between the first region and the sixth region and the hybridization between the second region and the seventh region ($\Delta G°_{nh-PC} + \Delta G°_{h-PC}$) is less than −15 kcal/mol.

12. The composition of claim 7 wherein the sum of the standard free energy of the hybridization between the third region and the fifth region and the hybridization between the between the fourth region and the second region ($\Delta G°_{nh-PC} + \Delta G°_{h-PC}$) is less than −15 kcal/mol.

* * * * *

UNITED STATES PATENT AND TRADEMARK OFFICE
CERTIFICATE OF CORRECTION

PATENT NO. : 10,900,079 B2
APPLICATION NO. : 15/174373
DATED : January 26, 2021
INVENTOR(S) : David Yu Zhang et al.

It is certified that error appears in the above-identified patent and that said Letters Patent is hereby corrected as shown below:

In the Claims

In Claim 1, Column 53, Line 52, delete "$\Delta°_{nh\text{-}PC}$" and insert --$\Delta G°_{nh\text{-}PC}$-- therefor.

In Claim 7, Column 55, Line 25, delete "$\Delta G°_{h\text{-}PC}$" and insert --$\Delta G°_{h\text{-}PC}$)-- therefor.

In Claim 7, Column 55, Line 37, delete "$\Delta G20_{nh\text{-}Pc}$" and insert --$\Delta G°_{nh\text{-}PC}$-- therefor.

In Claim 11, Column 56, Lines 31-32, delete "$\Delta G°_{nh\text{-}PC} + \Delta G°_{h\text{-}PC}$" and insert --$\Delta G°_{t\text{-}TC} + \Delta G°_{v\text{-}TC}$-- therefor.

Signed and Sealed this
First Day of June, 2021

Drew Hirshfeld
*Performing the Functions and Duties of the
Under Secretary of Commerce for Intellectual Property and
Director of the United States Patent and Trademark Office*